(12) United States Patent
An

(10) Patent No.: US 12,223,536 B2
(45) Date of Patent: Feb. 11, 2025

(54) METHOD FOR PROVIDING CUSTOMIZED COSMETIC PRODUCT SERVICE

(71) Applicant: LILLYCOVER CO., LTD., Daegu (KR)

(72) Inventor: Sun Hee An, Gyeongsan-si (KR)

(73) Assignee: LILLYCOVER CO., LTD., Daegu (KR)

( * ) Notice: Subject to any disclaimer, the term of this patent is extended or adjusted under 35 U.S.C. 154(b) by 231 days.

(21) Appl. No.: 17/908,353

(22) PCT Filed: Oct. 8, 2021

(86) PCT No.: PCT/KR2021/013892
§ 371 (c)(1),
(2) Date: Aug. 31, 2022

(87) PCT Pub. No.: WO2022/086004
PCT Pub. Date: Apr. 28, 2022

(65) Prior Publication Data
US 2023/0108573 A1   Apr. 6, 2023

(30) Foreign Application Priority Data

Oct. 19, 2020   (KR) .................... 10-2020-0135526

(51) Int. Cl.
*G06Q 30/0601*   (2023.01)
*A61B 5/00*   (2006.01)
(Continued)

(52) U.S. Cl.
CPC ......... *G06Q 30/0631* (2013.01); *A61B 5/441* (2013.01); *A61B 5/7465* (2013.01);
(Continued)

(58) Field of Classification Search
CPC .......... G06Q 30/0621; G06Q 30/0631; G06Q 50/04; G06Q 30/0601–0643;
(Continued)

(56) References Cited

U.S. PATENT DOCUMENTS 11,160,497 B1 * 11/2021 Hayman ............... A61B 5/6898
11,308,538 B1 *  4/2022 Pineau ............... G06Q 30/0282
(Continued)

FOREIGN PATENT DOCUMENTS

KR    10-2007-0006288 A    1/2007
KR       10-1444726 B1    9/2014
(Continued)

OTHER PUBLICATIONS

Chung, KY. "Effect of facial makeup style recommendation on visual sensibility." Multimedia Tools and Applications. vol. 71, pp. 843-853. (Year: 2013).*

(Continued)

*Primary Examiner* — Marissa Thein
*Assistant Examiner* — Katherine A Barlow
(74) *Attorney, Agent, or Firm* — Sughrue Mion, PLLC

(57) ABSTRACT

A method of providing customized cosmetic service according to an embodiment of the disclosure includes obtaining skin measurement information and skin input information of a user by using a user terminal, generating skin diagnosis information on a skin condition of the user based on the skin input information and the skin measurement information, generating recipe data for manufacturing customized cosmetics based on the skin diagnosis information, and manufacturing, by a customized cosmetic manufacturing apparatus, customized cosmetics based on the recipe data.

5 Claims, 21 Drawing Sheets

(51) Int. Cl.
*A61K 8/00* (2006.01)
*G06Q 50/04* (2012.01)

(52) U.S. Cl.
CPC ........... *A61K 8/00* (2013.01); *G06Q 30/0621* (2013.01); *G06Q 50/04* (2013.01)

(58) Field of Classification Search
CPC ............................ G06Q 30/0613–0619; G06Q 30/0641–0643; A61K 8/00; A61K 8/04–068; B01F 2101/21
See application file for complete search history.

(56) References Cited

U.S. PATENT DOCUMENTS

| | | | |
|---|---|---|---|
| 11,440,045 B2* | 9/2022 | Waldo | B05C 17/00583 |
| 2015/0202143 A1* | 7/2015 | Dubois | A61Q 19/007 |
| | | | 514/474 |
| 2015/0231582 A1* | 8/2015 | Schwartz | B01F 35/7174 |
| | | | 366/142 |
| 2016/0075738 A1* | 3/2016 | Ferrer Montiel | C07K 5/0819 |
| | | | 514/19.3 |
| 2017/0003268 A1* | 1/2017 | Astarita | H01J 49/0045 |
| 2017/0154372 A1* | 6/2017 | Balooch | B01F 33/846 |
| 2018/0211308 A1* | 7/2018 | Cheeks | G06Q 30/0613 |
| 2018/0285952 A1* | 10/2018 | Lu | B01F 29/10 |
| 2018/0368558 A1* | 12/2018 | Park | A45D 44/005 |
| 2019/0378187 A1* | 12/2019 | Lin | G06Q 10/063112 |
| 2021/0019711 A1* | 1/2021 | Romero | G06Q 10/1095 |

FOREIGN PATENT DOCUMENTS

| | | |
|---|---|---|
| KR | 10-2019-0050832 A | 5/2019 |
| KR | 10-2020-0002418 A | 1/2020 |
| KR | 10-2020-0069695 A | 6/2020 |

OTHER PUBLICATIONS

International Search Report for PCT/KR2021/013892 dated Jan. 27, 2022.

* cited by examiner

FIG. 4

METHOD FOR PROVIDING CUSTOMIZED COSMETIC PRODUCT SERVICE

CROSS REFERENCE TO RELATED APPLICATIONS

This application is a National Stage of International Application No. PCT/KR2021/013892 filed Oct. 8, 2021, claiming priority based on Korean Patent Application No. 10-2020-0135526 filed Oct. 19, 2020.

The disclosure relates to a method of providing a cosmetic service customized according to a skin diagnosis for each customer, and more particularly, to a method for providing a customized cosmetic service in which a cosmetic customized according to a skin diagnosis for each customer is prepared and provided and a skin care method using the same is provided.

BACKGROUND ART

Recently, various types of cosmetics recommended for use according to skin conditions such as dry skin or oily skin have been released. However, the skin condition of people may vary depending on various causes such as age, skin troubles, and genetic factors, and accordingly, the ingredients and amounts of cosmetic materials need to be adjusted depending on the user. Therefore, it is difficult to satisfy all users by simply classifying skin conditions into several conditions.

DESCRIPTION OF EMBODIMENTS

Technical Problem

According to embodiments of the disclosure, cosmetics customized according to skin diagnosis information for each customer are automatically manufactured, and continuous and real-time skin care services using the customized cosmetics are provided.

Technical Solution to Problem

A method of providing customized cosmetic service according to an embodiment of the disclosure includes obtaining skin measurement information and skin input information of a user by using a user terminal, generating skin diagnosis information on a skin condition of the user based on the skin input information and the skin measurement information, generating recipe data for manufacturing customized cosmetics based on the skin diagnosis information, and manufacturing, by a customized cosmetic manufacturing apparatus, customized cosmetics based on the recipe data.

Advantageous Effects of Disclosure

According to embodiments of the disclosure, cosmetics customized according to skin diagnosis information for each customer are automatically manufactured, and continuous and real-time skin care services using the customized cosmetics are provided.

BRIEF DESCRIPTION OF DRAWINGS

FIG. 4 is a diagram illustrating a screen on which skin input information is obtained according to an embodiment of the disclosure.

BEST MODE

Figure 1:
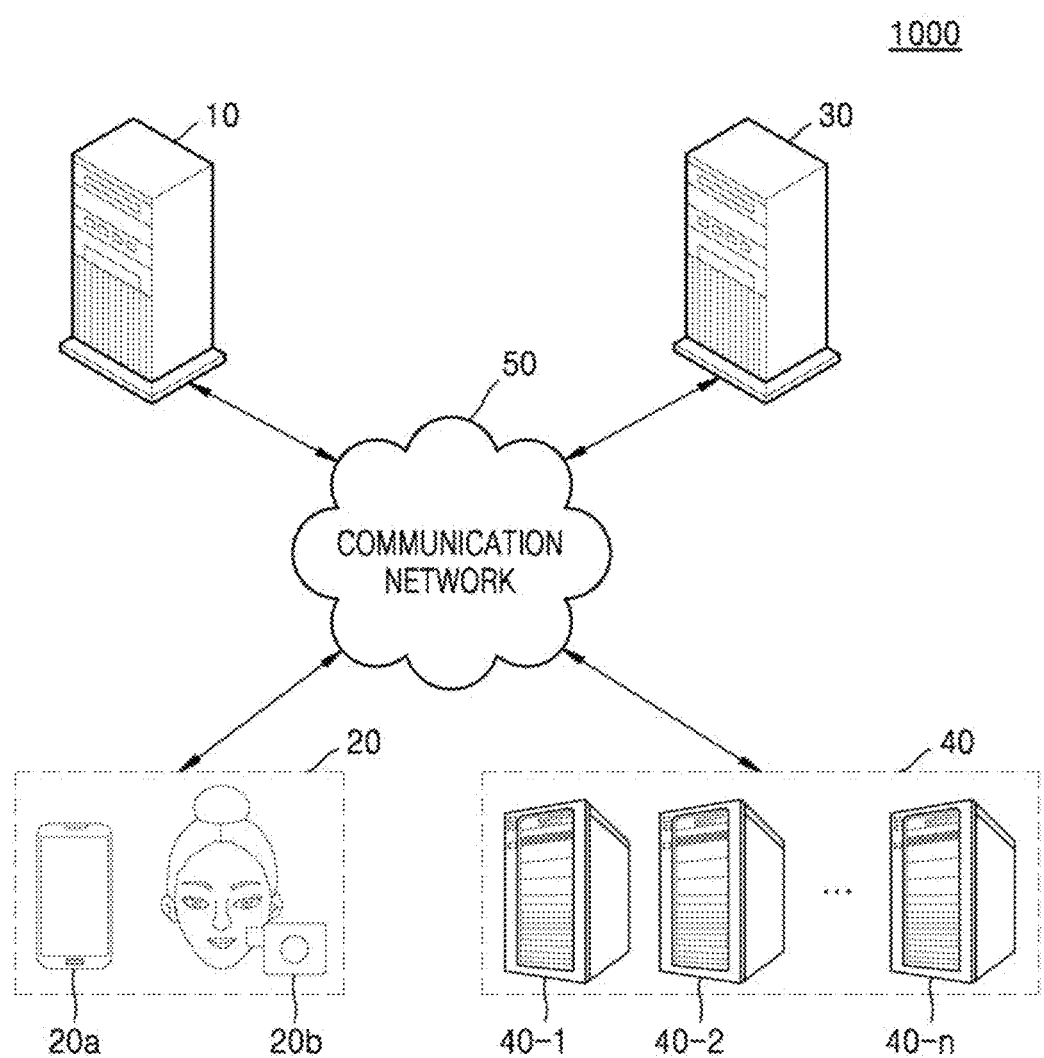
FIG. 1 is a diagram schematically illustrating the configuration of a system for providing a customized cosmetic service according to an embodiment of the disclosure.

A method of providing customized cosmetic service according to an embodiment of the disclosure includes obtaining skin measurement information and skin input information of a user by using a user terminal, generating skin diagnosis information on a skin condition of the user based on the skin input information and the skin measurement information, generating recipe data for manufacturing customized cosmetics based on the skin diagnosis information, and manufacturing, by a customized cosmetic manufacturing apparatus, customized cosmetics based on the recipe data.

The skin measurement information is obtained using a photographing part and a sensor part, and the skin input information is obtained through a user input on a selection interface displaying a diagnosis check item, wherein the diagnosis check item includes at least one of an oily type diagnosis item, a pigment type diagnosis item, a moisture type diagnosis item, a wrinkle type diagnosis item, a pore type diagnosis item, a trouble diagnosis item, and a sensitivity diagnosis item.

The generating the skin diagnosis information may include: generating quantitative data for each skin variable by quantifying, with respect to each skin variable, the skin input information and the skin measurement information; generating qualitative data including at least one of a skin type of the user, a detailed description of the skin type, care information suitable for the skin type, and skin age based on the skin measurement information and the skin input information; and providing a skin diagnosis certificate indicating at least one of the quantitative data and the qualitative data.

The generating the recipe data includes: manufacturing a customized base by determining a first base amount of a solubilized base and a second base amount of an emulsified base according to the skin diagnosis information, wherein the first amount of the customized base is calculated by adding the first base amount and the second base amount; determining whether to add a lipophilic component and a second amount according to the skin diagnosis information; and determining the type of effective component and a third amount, wherein the effective component includes a component that manages each of a whitening item, a moisturizing item, an elasticity item, a wrinkles item, an acne item, a soothing item, a sebum control item, and a pore reduction item, wherein transparency, texture, and formulation of customized cosmetics are determined based on at least one of the first amount, the second amount, and the third amount.

The customized cosmetic service providing method further includes providing a non-face-to-face skin coaching service, wherein the providing of the non-face-to-face skin coaching service includes: matching an expert for each user; obtaining coaching data generated by the expert based on the skin diagnosis information, the recipe data, and the manufactured customized cosmetic information; providing the coaching data to the user at a preset time and/or period; and calculating a coaching cost based on service evaluation information obtained from the user, and providing the coaching cost to a matched expert.

MODE OF DISCLOSURE

The present disclosure may be subjected to various changes and may have various embodiments. Accordingly, specific embodiments are illustrated in the drawings and described in detail in the detailed description. Effects and features of the disclosure, and a method for achieving the same will become apparent with reference to the embodiments described below in detail in conjunction with the drawings. However, the disclosure is not limited to the embodiments disclosed below and may be implemented in various forms.

Hereinafter, embodiments of the disclosure will be described in detail with reference to the accompanying drawings, and when described with reference to the drawings, the same or corresponding elements are given the same reference numerals, and the redundant description thereof will be omitted.

In the following embodiments, terms such as first, second, etc. are used for the purpose of distinguishing one element from another, not in a limiting sense. In the following examples, the singular expression includes the plural expression unless the context clearly dictates otherwise. In the following embodiments, terms such as "include" or "have" means that the features or elements described in the specification are present, and the possibility that one or more other features or elements will be added is not excluded in advance. In the drawings, the size of the elements may be exaggerated or reduced for convenience of description. For example, since the size and shape of each element shown in the drawings are arbitrarily indicated for convenience of description, the disclosure is not necessarily limited to the illustrated embodiment.

Figure 2:
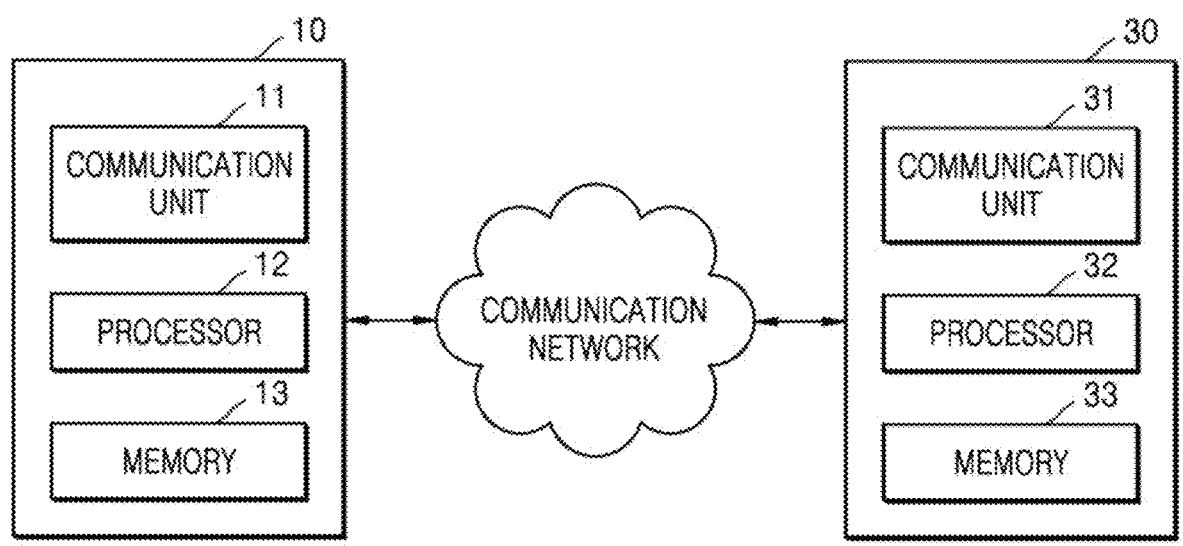
FIG. 2 is a diagram schematically illustrating the configuration of a skin diagnosis server and a customized cosmetics providing server, according to an embodiment of the disclosure.

Hereinafter, a system 1000 for providing a customized cosmetic service according to an embodiment of the disclosure (hereinafter, referred to as a 'service providing system 1000') will be described with reference to FIGS. 1 and 2. FIG. 1 is a diagram schematically illustrating the configuration of the system 1000 for providing a customized cosmetic service according to an embodiment of the disclosure, and FIG. 2 is a diagram schematically illustrating the configuration of a skin diagnosis server and a customized cosmetics providing server, according to an embodiment of the disclosure.

The service providing system 1000 may automatically manufacture cosmetics customized according to skin diagnosis information for each user (client), and provide continuous and real-time skin care services using the customized cosmetics. The service providing system 1000 may generate the skin diagnosis information from the skin-related information acquired for each user, and may generate recipe data for creating customized cosmetics for each user based on the skin diagnosis information. The service providing system 1000 may manufacture customized cosmetics according to a preset algorithm based on the recipe data, and provide continuous skin care services by generating, for example, skin history information and skin care information based on skin diagnosis information and recipe data. At this time, skin history information and skin care information are updated by accumulatively storing skin-related information generated before the time of generation and updating with newly generated information. The service providing system 1000 according to an embodiment of the disclosure may provide continuous as well as real-time updated skin diagnosis and care information.

The service providing system 1000 may include a skin diagnosis server 10, a measurement part 20, a service providing server 30, and a customized cosmetic manufacturing apparatus 40 (hereinafter referred to as 'cosmetic manufacturing apparatus 40'). The present embodiment will be described in detail with reference to FIG. 2.

The skin diagnosis server 10 and the service providing server 30 may include communication units 11 and 31, processors 12 and 32, and memories 13 and 33.

The communication units 11 and 31 may communicate with various types of external devices and servers according to various types of communication methods. The communication units 11 and 31 of the disclosure may be connected by a communication network 50 to exchange data with each other, but embodiments are not limited thereto, and some of elements 10, 20, 30, and 40 may be connected to a separate communication network 50 to communicate therewith.

The processors 12 and 32 may control servers 10 and 30 including a memory by using various programs stored in the memories 13 and 33. The processors 12 and 32 may include a microprocessor, a central processing unit (CPU), a processor core, a multiprocessor, an application-specific integrated circuit (ASIC), a field programmable circuit gate array (FPGA), but are not limited thereto.

First, the measurement part 20 may include at least one of a first user terminal 20a and a second user terminal 20b. The user terminal may refer to various types of information processing devices that mediate the user and the servers 10 and 30 so as to use various services provided by at least one of the skin diagnosis server 10 and the service providing server 30. For example, the user terminal may receive an interface for inputting or obtaining skin-related information from the servers 10 and 30 and provide the same to the user, and may obtain the user input corresponding thereto and transmits the same to the servers 10 and 30.

Such a user terminal may include at least one of the first user terminal 20a and the second user terminal 20b, as illustrated in FIG. 1. The skin-related information for each user may include skin measurement information and skin input information. The first user terminal 20a may be a device for obtaining skin input information from a user, and the second user terminal 20b may be a device for obtaining skin measurement information from the user. However, embodiments are not limited thereto. In an embodiment, the skin measurement information and the skin input information may all be obtained from either the first user terminal 20a or the second user terminal 20b. The first user terminal 20a and the second user terminal 20b may be the same type of device or different types of devices.

The processor 12 may obtain skin measurement information and skin input information, for each user, by using the first user terminal 20a and the second user terminal 20b.

An application linked to the skin diagnosis server 10 and/or the second user terminal 20b may be installed in the first user terminal 20a according to an embodiment of the disclosure. The first user terminal 20a may receive a first interface from the skin diagnosis server 10 and display the same thereon, and the skin diagnosis server 10 may obtain skin input information through a user input on the first interface. A method of obtaining skin input information will be described in more detail with reference to FIGS. 3 and 4 to be described later.

The second user terminal 20b according to an embodiment of the disclosure may include a photographing part and/or a sensor part, and the skin diagnosis server 10 may obtain skin measurement information through the photographing part and/or the sensor part. A method of obtaining skin measurement information will be described in more detail with reference to FIGS. 3, 5, and 6 to be described later. The second user terminal 20b may receive a first interface from the skin diagnosis server 10 and display the same thereon, and the skin diagnosis server 10 may obtain skin input information through a user input on the first interface.

The processor 12 may generate skin diagnosis information on each user's skin condition based on the skin-related information obtained from the measurement part 20, and transmit the same to a service providing server 30. The generating and providing skin diagnosis information will be described in more detail with reference to FIGS. 3 and 7 to be described later.

Thereafter, the processor 32 of the service providing server 30 may generate recipe data for manufacturing cosmetics customized for each user based on the skin diagnosis information. A method of generating recipe data will be described in more detail with reference to FIG. 8 to be described later.

The memories 13 and 33 may temporarily or permanently store data processed by the servers 10 and 30 each including a memory. The memories 13 and 33 may include a permanent mass storage device such as a random access memory (RAM), a read only memory (ROM), and a disk drive, but the scope of the disclosure is limited thereto. For example, the memories 13 and 33 may temporarily and/or permanently store parameters and/or weights constituting the learned artificial neural network.

A customized cosmetic manufacturing apparatus 40 may be connected to the skin diagnosis server 10, the measurement part 20, and the service providing server 30 through a communication network 50 to exchange data with each other, so as to manufacture customized cosmetics. The cosmetic manufacturing apparatus 40 may manufacture customized cosmetics based on recipe data received from the skin diagnosis server 10 and/or the measurement part 20.

The cosmetic manufacturing apparatus 40 may include a plurality of cosmetic manufacturing apparatuses 40-1, 40-2, . . . , 40-n, which are provided in different places to be supplied and sold at a place according to the user's need according to the user's skin measurement information and order information. The configuration and function of the cosmetic manufacturing apparatus 40 will be described in more detail with reference to FIGS. 12 to 20 to be described later.

The communication network 50 may be defined as one or more data links capable of transmitting and receiving data between electronic devices and/or servers. The communication network 50 may be, for example, a wired network, such as local area networks (LANs), wide area networks (WANs), metropolitan area networks (MANs), integrated service digital networks (ISDNs), or a wireless network, such as wireless LANs, code division multiple access (CDMA), Bluetooth, satellite communication, etc, but the scope of the disclosure is not limited thereto.

Although not shown in FIG. 2, each of the measurement part 20 and the cosmetic manufacturing apparatus 40 shown in FIG. 1 may also include a communication unit, a processor, and a memory. According to a need, the server or processor described according to the disclosure may be implemented as a single server or a single processor, or implemented as a plurality of separate servers or processors. For example, the processor 12 of the skin diagnosis server 10 may be provided as an element included in the measurement part 20, such as a processor of the measurement part 20, and according to embodiments, as the processor 32 of the service providing server 30. The processor 32 of the service providing server 30 may be provided as a processor in the cosmetic manufacturing apparatus 40.

Figure 3:
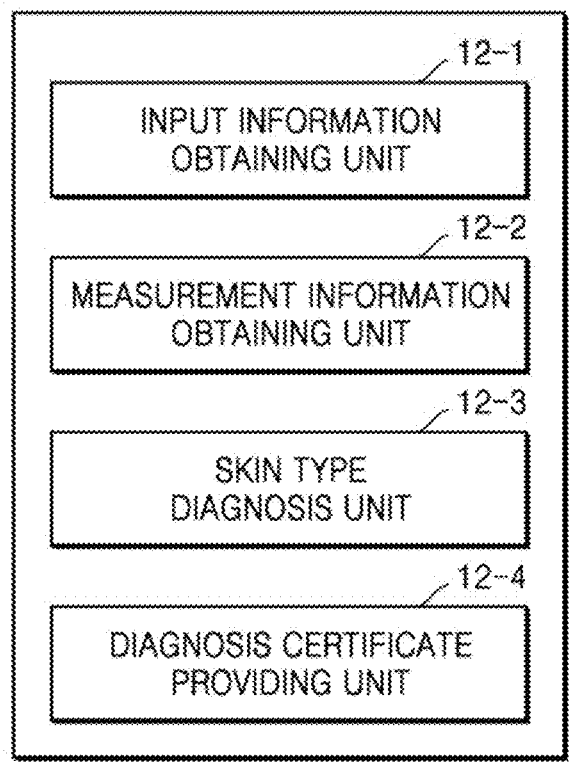
FIG. 3 is a diagram schematically illustrating a functional configuration of a processor of a skin diagnosis server according to an embodiment of the disclosure.

FIG. 3 is a diagram schematically illustrating a functional configuration of a processor of a skin diagnosis server according to an embodiment of the disclosure. The processor 12 of the skin diagnosis server 10 may include an input information obtaining unit 12-1, a measurement information obtaining unit 12-2, a skin type diagnosis unit 12-3, and a diagnosis certificate providing unit 12-4.

Figure 4:
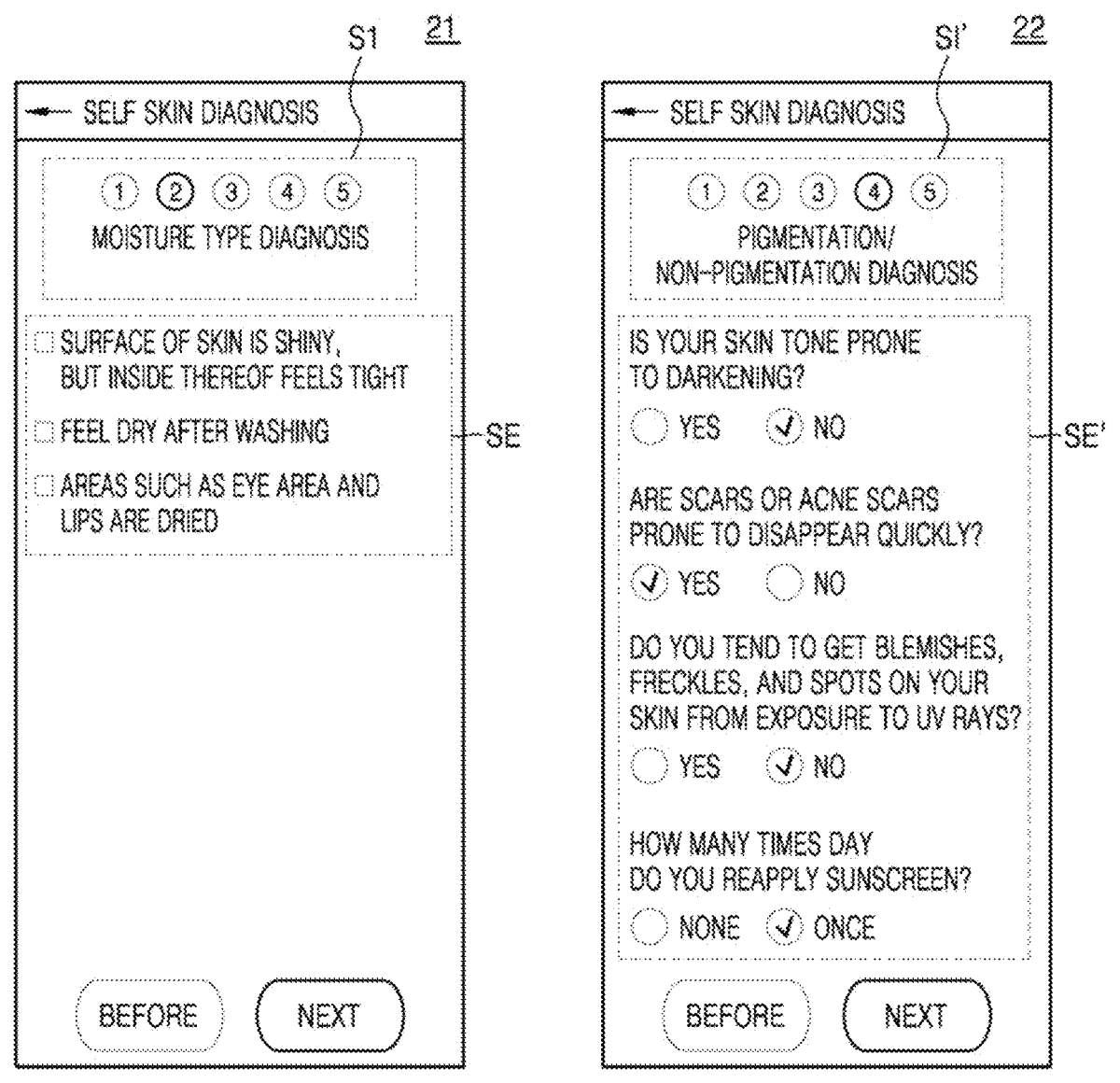

The input information obtaining unit 12-1 may obtain skin input information for each user from the measurement part 20. The present embodiment will be described in detail with reference to FIG. 4. FIG. 4 is a diagram illustrating an example screen on which skin input information is obtained according to an embodiment of the disclosure. The example screen of FIG. 4 may be a screen displayed on the user terminal of the measurement part 20, in particular, the display unit of the first user terminal 20*a*. Example screens 21 and 22 are input screens at different time points.

The processor 12 may provide questionnaire interfaces SI and SI' and selection interfaces SE and SE' displayed on the example screen of FIG. 4. The questionnaire interfaces SI and SI' may display various diagnosis check items for diagnosing a user's skin condition. The diagnosis check items may include at least one selected from an item for oily type diagnosis, an item for water type diagnosis, an item for sensitivity/resistance diagnosis, an item for pigmentation/non-pigmentation diagnosis, and an item for elasticity/wrinkle diagnosis. The selection interfaces SE and SE' may be variously configured according to each diagnosis check item. For example, the selection interfaces SE and SE' are provided in various ways, for example, checking only the corresponding questionnaire as shown in the example screen 21, or selecting the corresponding options such as yes, no, and number of times as shown in the example screen 22.

In this way, the input information obtaining unit 12-1 may obtain the skin input information of the user through the user input on the selection interfaces SE and SE' for the selected diagnosis check items.

In FIG. 4, an example screen is displayed on the user terminal. However, embodiments are not limited thereto. In some embodiment, an example screen is displayed on the display unit of the kiosk terminal, and the user skin input information may be obtained through the kiosk.

Figure 5:
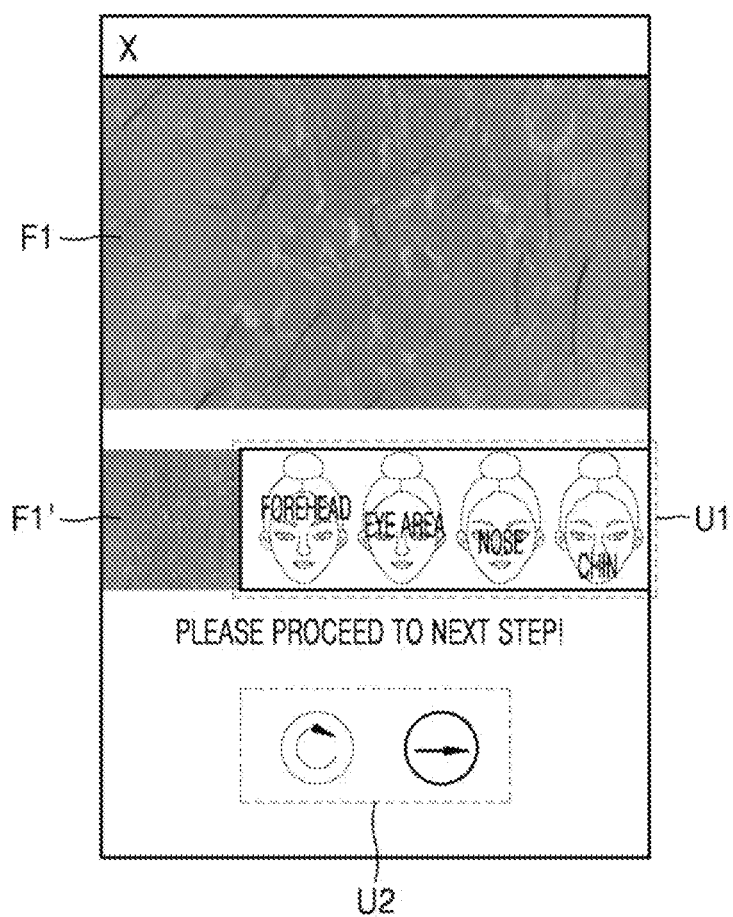
FIGS. 5 and 6 are diagrams illustrating a screen on which skin measurement information is obtained according to an embodiment of the disclosure.
Figure 6:
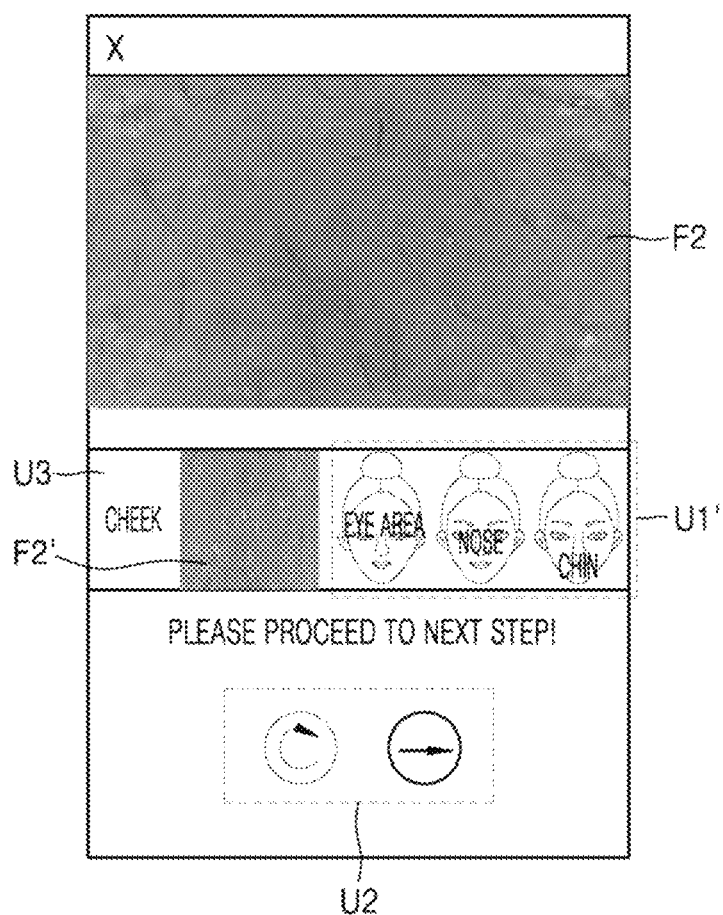

The measurement information obtaining unit 12-2 may obtain skin measurement information for each user from the measurement part 20. The present embodiment will be described in detail with reference to FIGS. 5 and 6. FIGS. 5 and 6 are diagrams illustrating a screen on which skin measurement information is obtained according to an embodiment of the disclosure. Example screens 23 and 24 of FIGS. 5 and 6 may be screens displayed on the user terminal of the measurement part 20, in particular, the display unit of the first user terminal 20*a*. The example screens 23 and 24 are screens at different time points.

The processor 12 may provide various interfaces displayed on the example screens 23 and 24 of FIGS. 5 and 6 and images obtained from the measurement part 20. First, on the example screen 23 of FIG. 5, a first captured image F1, a first obtained image F1', a first interface U1, and a second interface U2 are displayed. The first captured image F1 of FIG. 5 may be a captured image of a part, for example, a cheek. The first captured image F1 captured by the photographing part is completed as the first obtained image F1' and is stored in the memory 13, and the first obtained image F1' may be displayed in FIG. 5. On one side of the first obtained image F1', the first interface U1, which allows the selection of the rest of the face except for the part of the face of which in image is captured, is displayed. The first interface U1 may also be referred to as a part selection interface. When the first obtained image F1' is obtained, a second interface U2 is activated, and the processor 12 may receive a user input signal for the second interface U2 and display the example screen 24 of FIG. 6.

Referring to FIG. 6, the displayed interface and the displayed image are almost the same as in FIG. 5, except that the part of the face, of which an image is obtained, is changed. Hereinafter, the differences will be mainly described.

The third interface U3 may be an interface implemented by overlapping the first obtained image F1' of 'cheek' obtained in FIG. 5 and an image including the text 'cheek', which is a portion corresponding to the first obtained image F1'. The example screen 24 of FIG. 6 is a screen for obtaining skin measurement information on a 'forehead' of the first interface U1 shown in FIG. 5. The second captured image F2 is a captured image of the 'forehead'. The second captured image F2 captured by the photographing part is completed as a second obtained image F2' and is stored in the memory 13, and the second obtained image F2' is displayed in FIG. 6. On one side of the second obtained image F2', the first interface U1', which allows the selection of the rest of the face except for the part of the face of which in image is captured, is displayed. When the second obtained image F2' is obtained, the second interface U2 is activated again, and the processor 12 may receive a user input signal for the second interface U2 and display the example screen 24 for obtaining skin measurement information on the next part of the face.

Although the skin measurement information obtained by the sensor part is not shown, information on skin impedance and roughness of the skin surface may be obtained, which is then processed through data processing processes such as quantification and charting to generate skin diagnosis information to be described later. Accurate and detailed real-time skin diagnosis and skin care information, for each user, may be provided by analyzing, through quantification algorithm or the like, high-resolution enlarged images of each part of the face through captured images F1 and F2 and skin measurement information such as skin impedance obtained by the sensor part.

In this way, the measurement information obtaining unit 12-2 may obtain the user's skin measurement information through a user input to the part selection interface and a captured image obtained by the photographing part and/or sensor part of the measurement part 20.

Referring to FIG. 3, the skin type diagnosis unit 12-3 may diagnose a detailed type of skin by using quantitative data and/or qualitative data generated based on skin-related information obtained by the input information obtaining unit 12-1 and the measurement information obtaining unit 12-2. Thereafter, a skin diagnosis certificate may be provided through a user terminal based on data obtained through the diagnosis certificate providing unit 12-4 and the skin type diagnosis unit 12-3.

Figure 7:
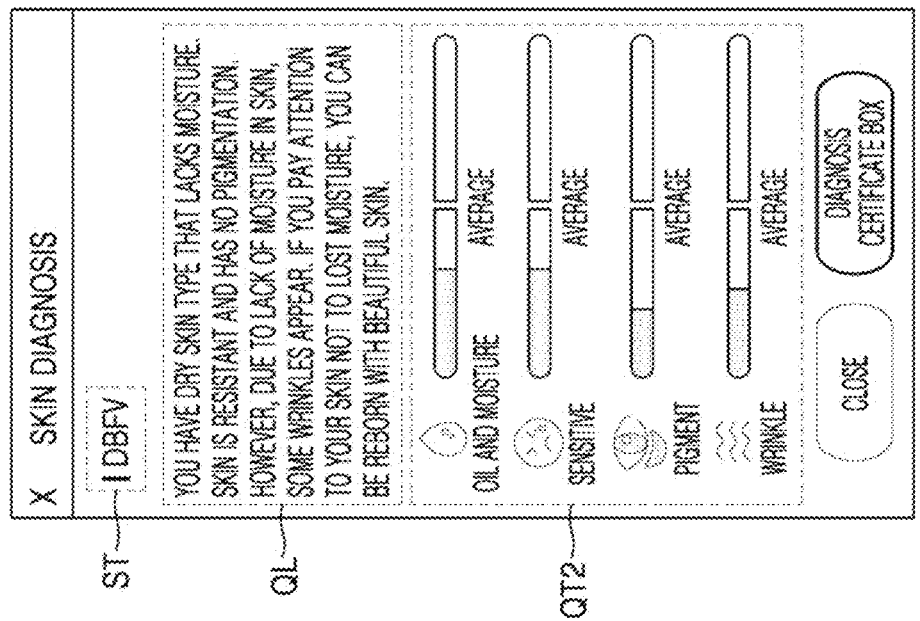
FIG. 7 is a diagram illustrating an example screen of a skin diagnosis certificate generated by generating skin diagnosis information according to an embodiment of the disclosure.
Figure 7:
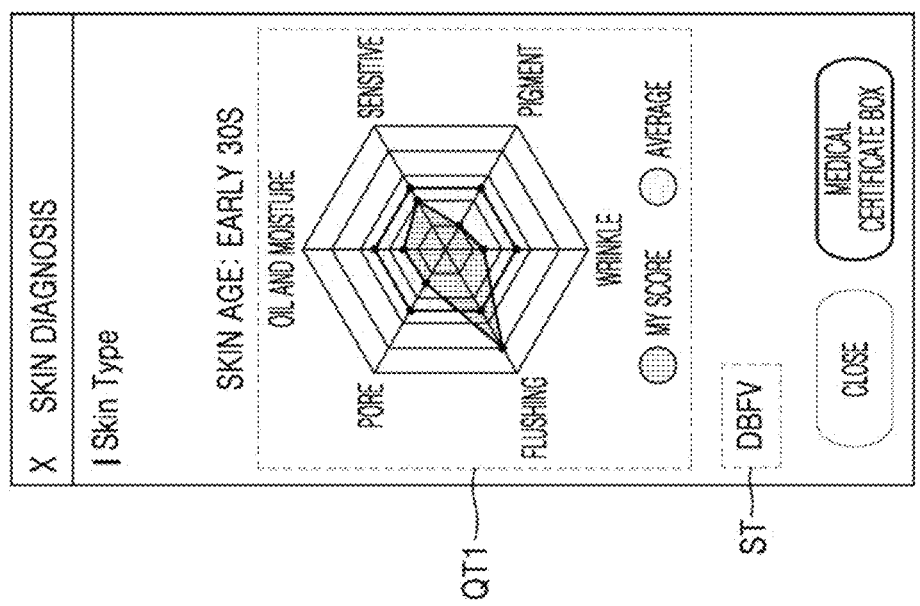

Hereinafter, the present embodiment will be described with reference to FIG. 7. FIG. 7 is a diagram illustrating an example screen on which a skin diagnosis certificate is displayed, generated by generating skin diagnosis information according to an embodiment of the disclosure.

The skin type diagnosis unit 12-3 may generate quantitative data for each skin variable by quantifying, with respect to each skin variable, the skin input information and the skin measurement information. The skin variable may include various variables that can be derived in relation to the diagnosis check items described above, for example, as shown in FIG. 7, pores, redness, wrinkles, pigmentation, sensitivity, and oil and moisture variables. However, the skin variable is not limited thereto, and may be variously set and selected within a range that is a reference for determining the type of a skin.

Examples of quantitative data QT are shown on example screens 25 and 26 of FIG. 7. The quantitative data QT may be displayed as a table in which user scores calculated for each skin variable are compared with average scores of other users stored in the memory 13. For example, quantitative data QT may include tabular data QT1 in which compared to the average for each skin variable, the user score can be seen at a glance, and bar graph data QT2 in which a separate graph is provided for each skin variable. The visualization method for expressing quantitative data QT is not limited thereto, and may be modified variously as long as the user understands his or her skin condition.

In addition, the skin type diagnosis unit 12-3 may generate qualitative data including at least one of a user's skin type, a detailed description of the determined skin type, care information suitable for the skin type, and skin age based on skin input information and skin measurement information. Referring to FIG. 7, a skin type ST and a detailed description QL, and the like are shown as examples of qualitative data. The skin type ST may be determined by giving weights according to preset standards to scores calculated for each skin variable. The detailed description QL may include a description corresponding to the skin type ST determined accordingly and a simple skin care method.

The diagnosis providing unit 12-4 may generate a skin diagnosis document as shown in FIG. 7 displaying at least one of the quantitative data and the qualitative data, and provide it through various user terminals. The configuration of the skin diagnosis certificate is not limited to that shown in FIG. 7, and may be any configuration that easily and efficiently provides information on skin conditions to the user.

Figure 8:
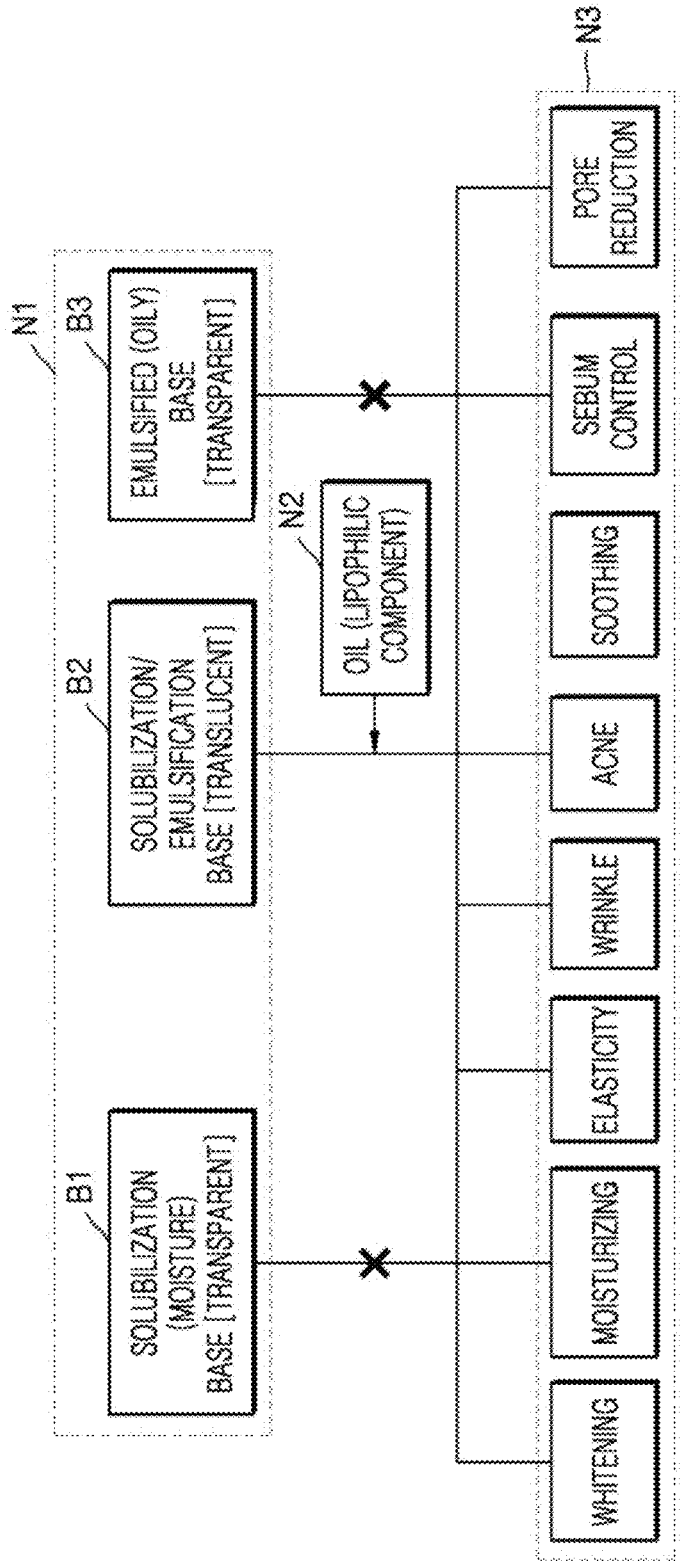
FIG. 8 is a diagram for explaining a method of generating recipe data according to an embodiment of the disclosure.

FIG. 8 is a diagram for explaining a method of generating recipe data according to an embodiment of the disclosure.

The processor 32 of the service providing server 30 may receive skin diagnosis information from the skin diagnosis server 10. The skin diagnosis information may be a concept including the quantitative data and the qualitative data. The processor 32 can manufacture customized base N1 by determining the first base amount of the solubilized base and the second base amount of the emulsified base according to skin diagnosis information. A first amount of the customized base N1 may be calculated by adding the first base amount and the second base amount. For example, the customized base N1 is, as shown in FIG. 8, may include a solubilized (moisture) base B1 determined only by the first base amount, an intermediate (solubilization/emulsification) base B2 based on the first base amount and the second base amount, and an emulsified base B3 determined only by the second base amount. In this case, the first base amount and the second base amount may be determined according to the skin type ST determined by the skin diagnosis server 10 and a skin variable included in the skin type ST. Transparency may decrease in the order from the solubilized base B1, the intermediate base B2, and the emulsified base B3, that is, as the ratio of the second base amount to the first base amount is increased.

The processor 32 may determine whether to add a lipophilic component N2 and a second amount thereof, according to skin diagnosis information. The lipophilic component may be an oil. Specifically, the lipophilic component N2 may be an optional component whose addition is determined according to the oily type diagnosis result, and when determined as being added, the second amount of oil may be determined for each preset step.

The processor 32 may determine the type of effective component N3 and a third amount thereof according to skin diagnosis information. The effective component may include a component that manages each of a whitening item, a moisturizing item, an elasticity item, a wrinkles item, an acne item, a soothing item, a sebum control item, and a pore reduction item. The processor 32 may select a required effective component N3 from among a plurality of effective component N3 according to the skin type ST for each user determined by the skin diagnosis server 10 and a skin variable included in the skin type ST, and may determine a third amount for the selected effective component N3. The third amount may be determined according to the selected skin type ST and a ratio obtained by comparing scores calculated according to various skin variables. For example, when the score for dryness and aging variables is relatively high in the skin type ST, the third amount of moisturizing and wrinkle function components from among effective component N3, may be determined to be high. In an embodiment, when the score for the oily variable is high, a trouble or acne functional component is selected from among the effective component N3, and the third amount therefor may be determined to be high.

Thereafter, the processor 32 may finally generate recipe data based on at least one of the first amount, the second amount, and the third amount. Thereafter, the cosmetic manufacturing apparatus 40 may manufacture customized cosmetics based on the recipe data. In the customized cosmetic, transparency, viscosity, texture, and formulation may be variously determined based on at least one of the first amount, the second amount, and the third amount.

Although not shown, the skin diagnosis server 10 and/or the service providing server 30 may further generate skin history information and skin care information for a user based on recipe data. The skin care information may include at least one of moisture care and UV care, and may further provide information on scalp care.

In this case, the processors 12 and 32 may generate the skin diagnosis information and recipe data using the learned artificial neural network. At this time, the artificial neural network may be a neural network learned using skin-related information of a plurality of users of various races, and may be updated with skin-related information obtained by new users in real time to provide accurate skin diagnosis/care information in real time.

As described above, according to embodiments of the disclosure, cosmetics customized according to skin diagnosis information for each customer can be automatically manufactured, and the continuous and real-time skin care services using the customized cosmetics can be provided.

Figure 9:
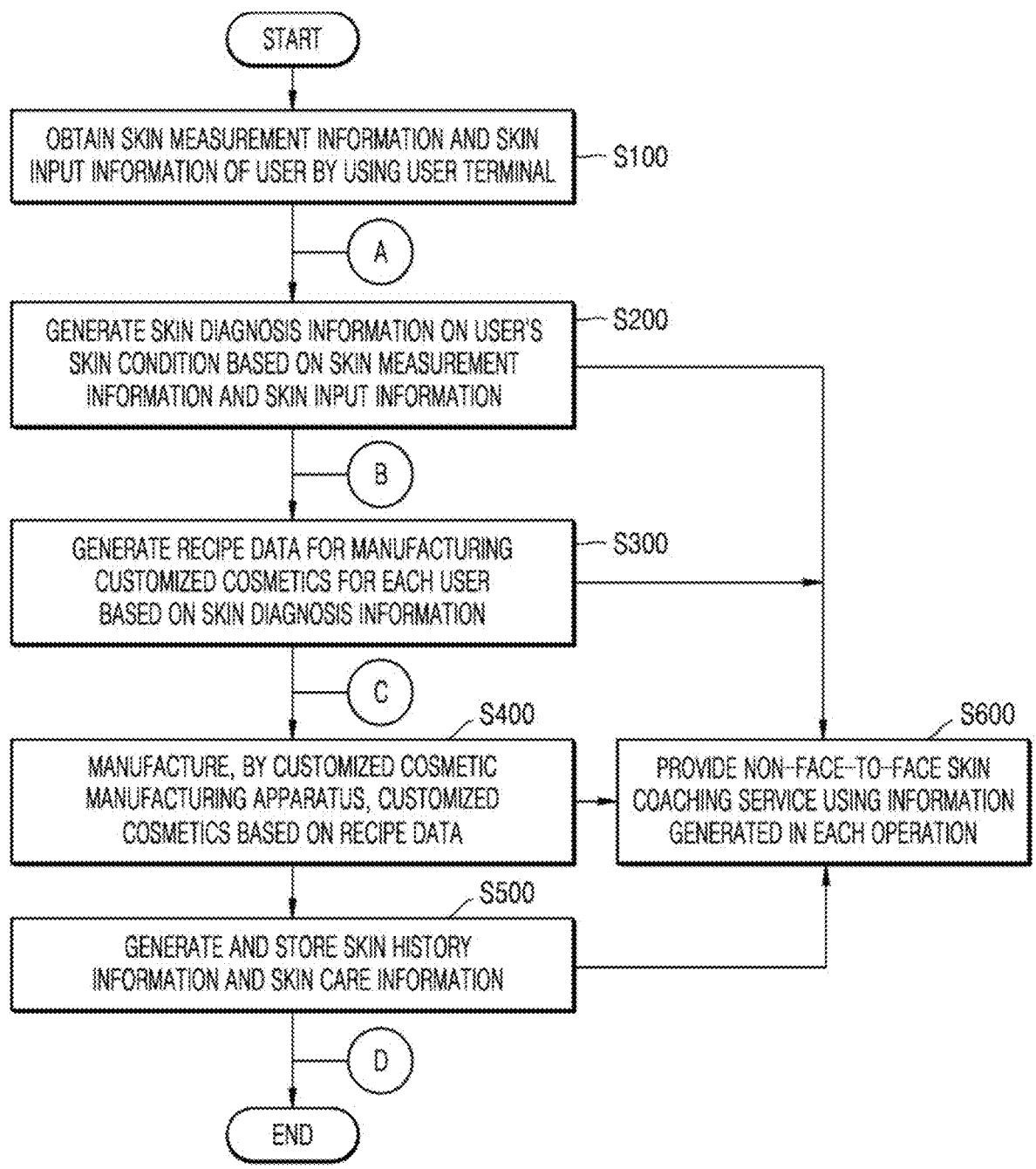
FIG. 9 is a flowchart illustrating a method of providing a customized cosmetic service according to an embodiment of the disclosure.

FIG. 9 is a flowchart for explaining a method of providing a customized cosmetic service according to an embodiment of the disclosure (hereinafter, referred to as a 'service providing method'). A service providing method according to an embodiment of the disclosure may include the following operations.

The skin diagnosis server 10 may obtain the skin measurement information and skin input information of the user by using the user terminal (S100).

Thereafter, the skin diagnosis server 10 may generate skin diagnosis information on the user's skin condition based on skin-related information including the skin input information and the skin measurement information (S200). The operation S200 will be described in more detail with reference to FIG. 10 to be described later.

The service providing server 30 may generate recipe data for manufacturing customized cosmetics for each user based on the skin diagnosis information (S300). The operation S300 will be described in more detail with reference to FIG. 11 to be described later.

Thereafter, the customized cosmetic manufacturing apparatus 40 may receive recipe data from the service providing server 30 and manufacture customized cosmetics based on the recipe data (S400).

In this case, the skin measurement information may be obtained using a photographing part and/or a sensor part of the user terminal included in the measurement part 20. Skin input information may be obtained by user input on a selection interface that displays diagnosis check items, wherein the diagnosis check items may include at least one of an oily type diagnosis item, a water type diagnosis item, a sensitivity/resistance diagnosis item, a pigmentation/non-pigmentation diagnosis item, and an elasticity/wrinkle item.

The service providing method of the disclosure may further include generating skin history information and skin care information for the user based on recipe data by using the skin diagnosis server 10 and/or the service providing server 30 and storing the same (S500). In this case, the skin care information may include at least one of recommended cosmetics such as moisture care, UV care, and mask pack, but is not limited thereto, and may include various information necessary for skin care.

The service providing method of the disclosure includes providing a non-face-to-face skin coaching service by using at least one piece of information from among the information generated in the respective operations (S200, S300, S400, and S500) (S600). The operation S600 will be described in more detail with reference to FIG. 12 to be described later.

Figure 10:
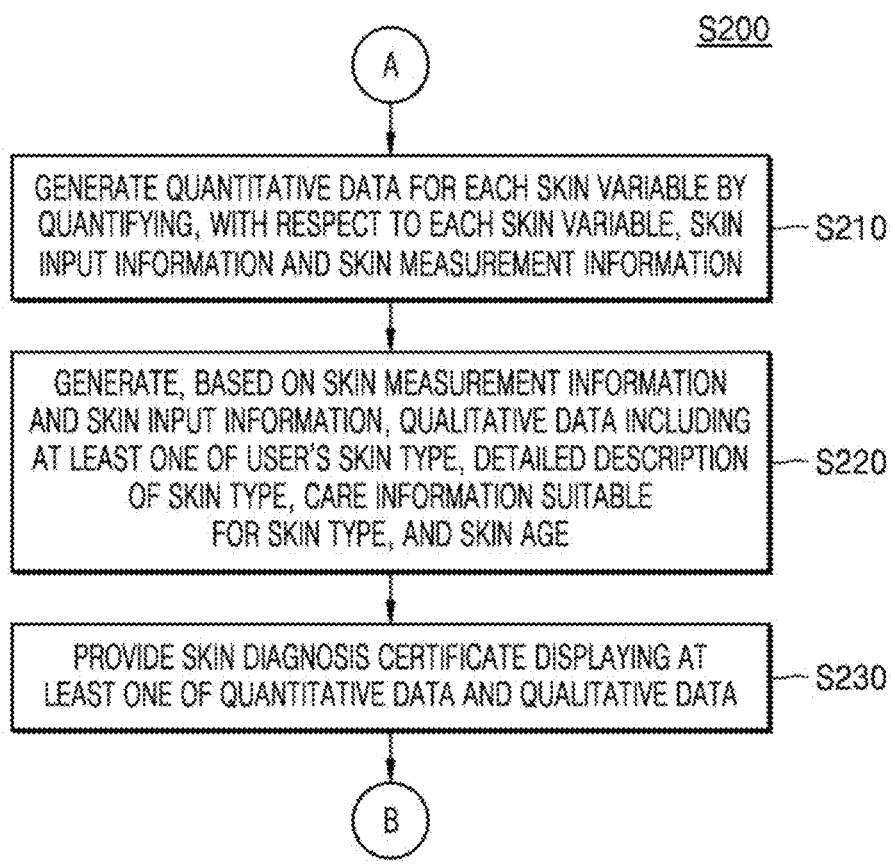
FIG. 10 is a flowchart for explaining in more detail some operations of a method for providing a customized cosmetic service according to an embodiment of the disclosure.

FIG. 10 is a flowchart for explaining in more detail the operation (S200) of a method for providing a customized cosmetic service according to an embodiment of the disclosure. The generating the skin diagnosis information (S200) may include operations to be described later.

The skin diagnosis server 10 may generate quantitative data for each skin variable by quantifying, with respect to each skin variable, the skin input information and the skin measurement information (S210). The skin type ST for each user may be determined based on the quantitative data.

In addition, the skin diagnosis server 10 may generate, based on the skin measurement information and the skin input information, qualitative data including at least one of the user's skin type, detailed description of the skin type, care information suitable for the skin type, and skin age (S220).

Thereafter, the skin diagnosis server 10 may provide a skin diagnosis certificate displaying at least one of the quantitative data and the qualitative data (S230).

Figure 11:
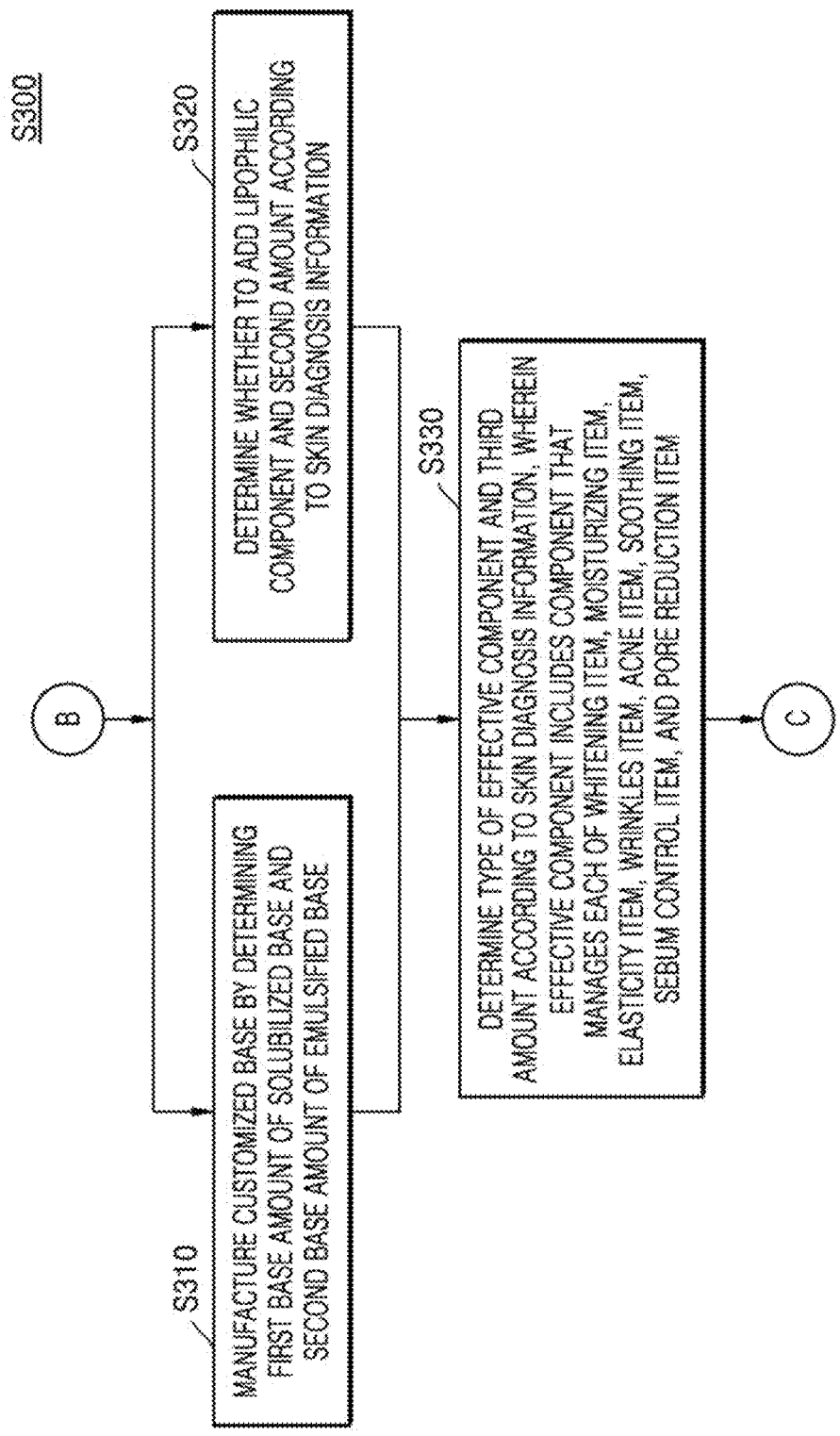
FIG. 11 is a flowchart for explaining in more detail some operations of a method for providing a customized cosmetic service according to an embodiment of the disclosure.

FIG. 11 is a flowchart for explaining in more detail an operation (S300) of a method for providing a customized cosmetic service according to an embodiment of the disclosure. The generating recipe data (S300) may include the following operations.

The service providing server 30 may manufacture a customized base N1 by determining the first base amount of the solubilized base and the second base amount of the emulsified base according to the skin diagnosis information generated by the skin diagnosis server 10 (S310). The first amount of the customized base N1 may be calculated by adding the first base amount and the second base amount.

The service providing server 30 may determine whether to add the lipophilic component N2 and a second amount thereof, according to skin diagnosis information (S320). The lipophilic element may be an oil. Specifically, the lipophilic element (N2) may be an optional element whose addition is determined according to the oily type diagnosis result, and when it is determined to be added, the second amount of the oil may be determined in preset steps.

Thereafter, the type of effective component N3 and a third amount thereof are determined according to skin diagnosis information. The effective component may include a component that manages each of a whitening item, a moisturizing item, an elasticity item, a wrinkles item, an acne item, a soothing item, a sebum control item, and a pore reduction item (S330).

Finally, the transparency, viscosity, texture, and formulation of the customized cosmetics manufactured by the cosmetic manufacturing apparatus 40 may be variously determined based on at least one of the first amount, the second amount, and the third amount.

Figure 12:
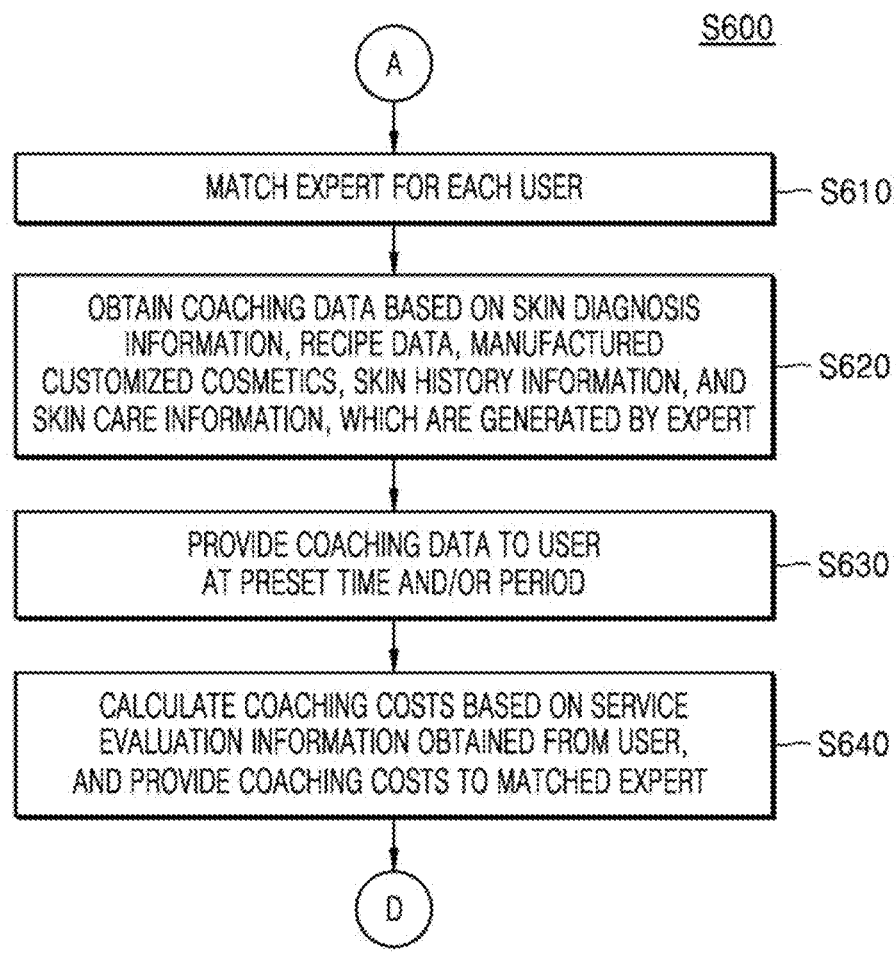
FIG. 12 is a flowchart illustrating a skin coaching service method according to an embodiment of the disclosure.

FIG. 12 is a flowchart illustrating a skin coaching service method according to an embodiment of the disclosure. The providing the non-face-to-face skin coaching service (S600) may include the following operations.

An expert may be matched with each user (S610). In this case, an expert who is highly consistent with a user request signal may be matched by using the expert information stored in the memory 33 and the user request signal. Experts to users may be either one-to-one or one-to-many.

Thereafter, the service providing server 30 may obtain coaching data generated by an expert based on skin diagnosis information, recipe data, manufactured customized cosmetics, skin history information, and skin care information (S620). The matched expert may generate coaching data by using at least one of the information generated in each of the operations (S200, S300, S400, and S500), and may provide the same to the service providing server 30. In this case, the coaching data may be configured based on these pieces of information and may include skin habit information that is optimized for the user.

Thereafter, the coaching data may be provided to the user at a preset time and/or period (S630). The coaching data may be provided through the user terminal 20a, etc., and by providing the coaching service at a preset time/period, the user may receive a regular and continuous customized skin care service.

Thereafter, the coaching costs may be calculated based on the service evaluation information obtained from the user, and the coaching costs may be provided to the matched expert (S640). The service evaluation information may be a score assigned to each preset evaluation item. The coaching costs may be calculated according to a cost calculation algorithm to which a preset lower limit amount, an upper limit amount, and a differential amount for each score section are applied in proportion to the score.

The following operations may be performed by the processor 32 of the service providing server 30, but may also be performed by a separate server if necessary.

Hereinafter, a cosmetic manufacturing apparatus 40 according to an embodiment of the disclosure will be described with reference to FIGS. 13 to 21.

Figure 13:
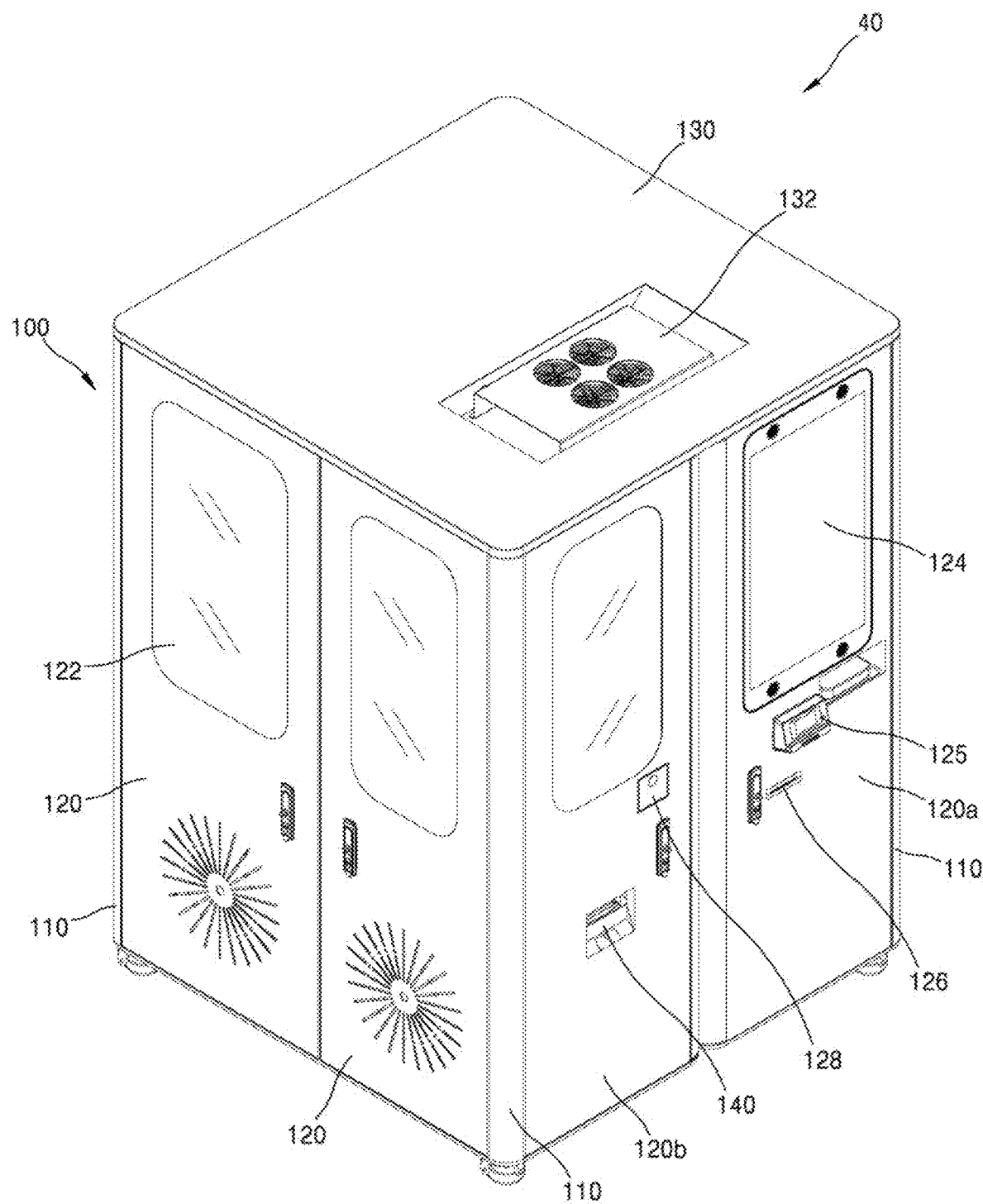
FIG. 13 is a perspective view schematically illustrating an apparatus for manufacturing customized cosmetics according to an embodiment of the disclosure.
Figure 14:
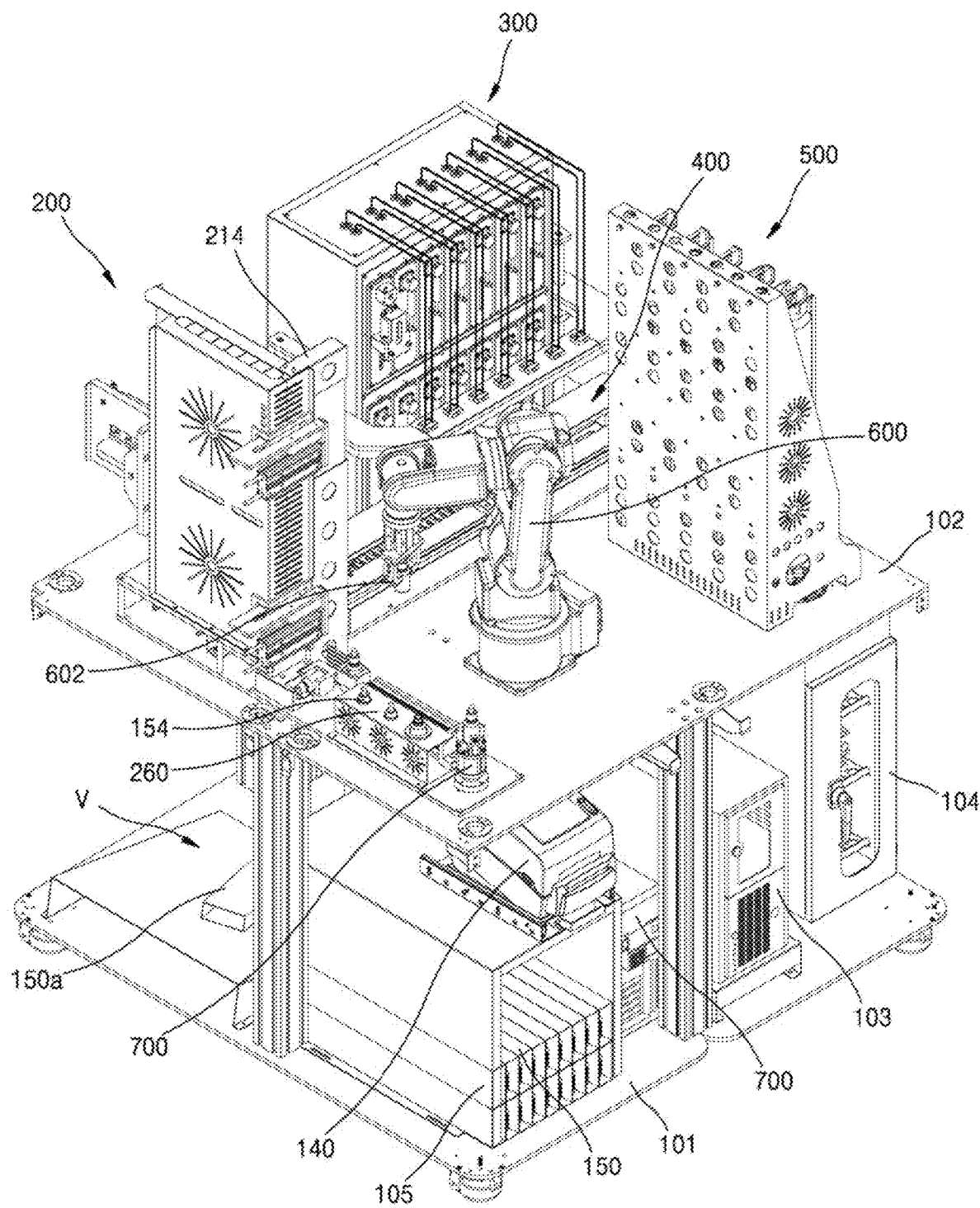
FIG. 14 is a perspective view schematically illustrating a part of the apparatus for manufacturing customized cosmetics of FIG. 13.
Figure 15:
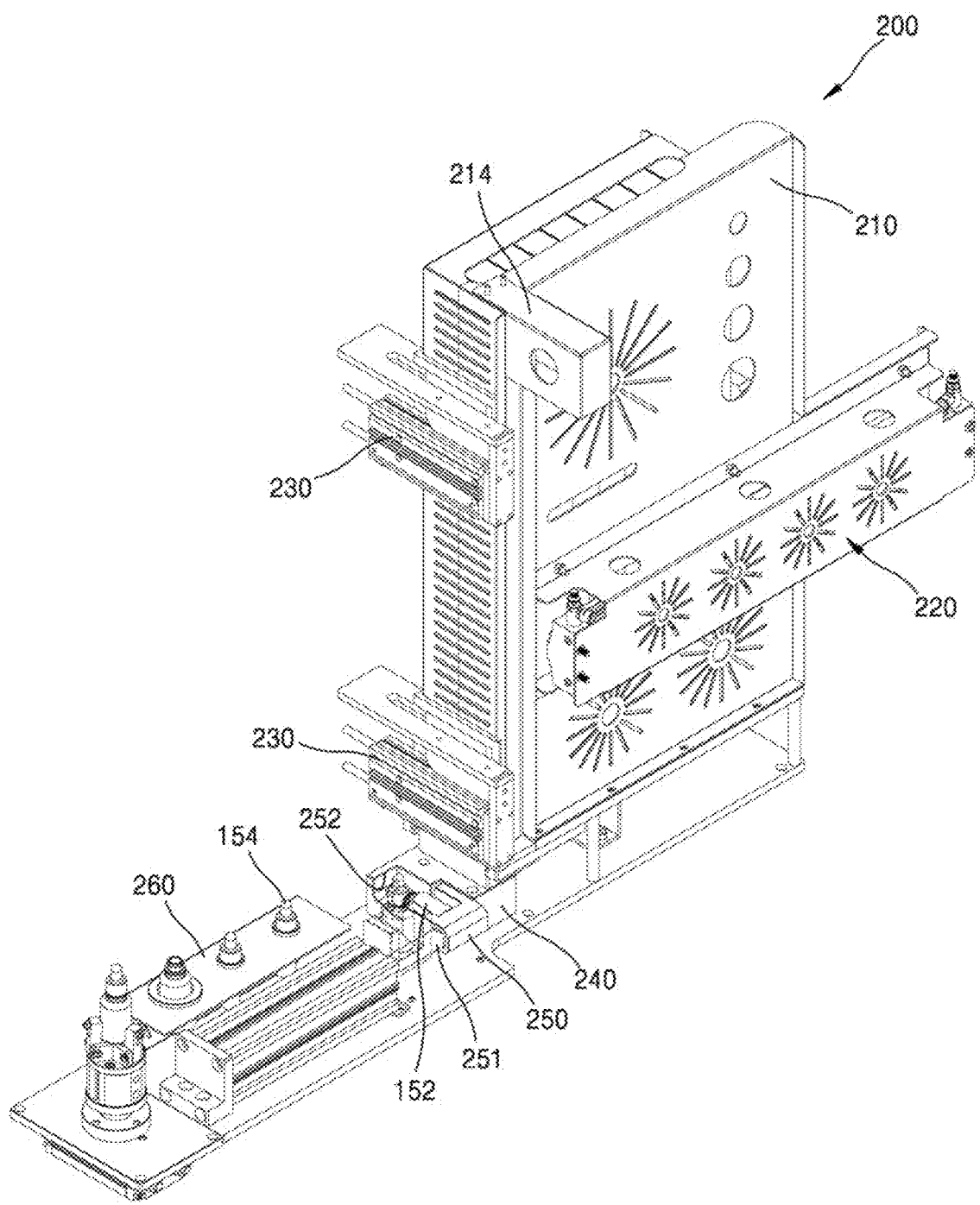
FIGS. 15 and 16 are perspective views schematically illustrating a container supply part of the apparatus for manufacturing customized cosmetics of FIG. 13.
Figure 16:
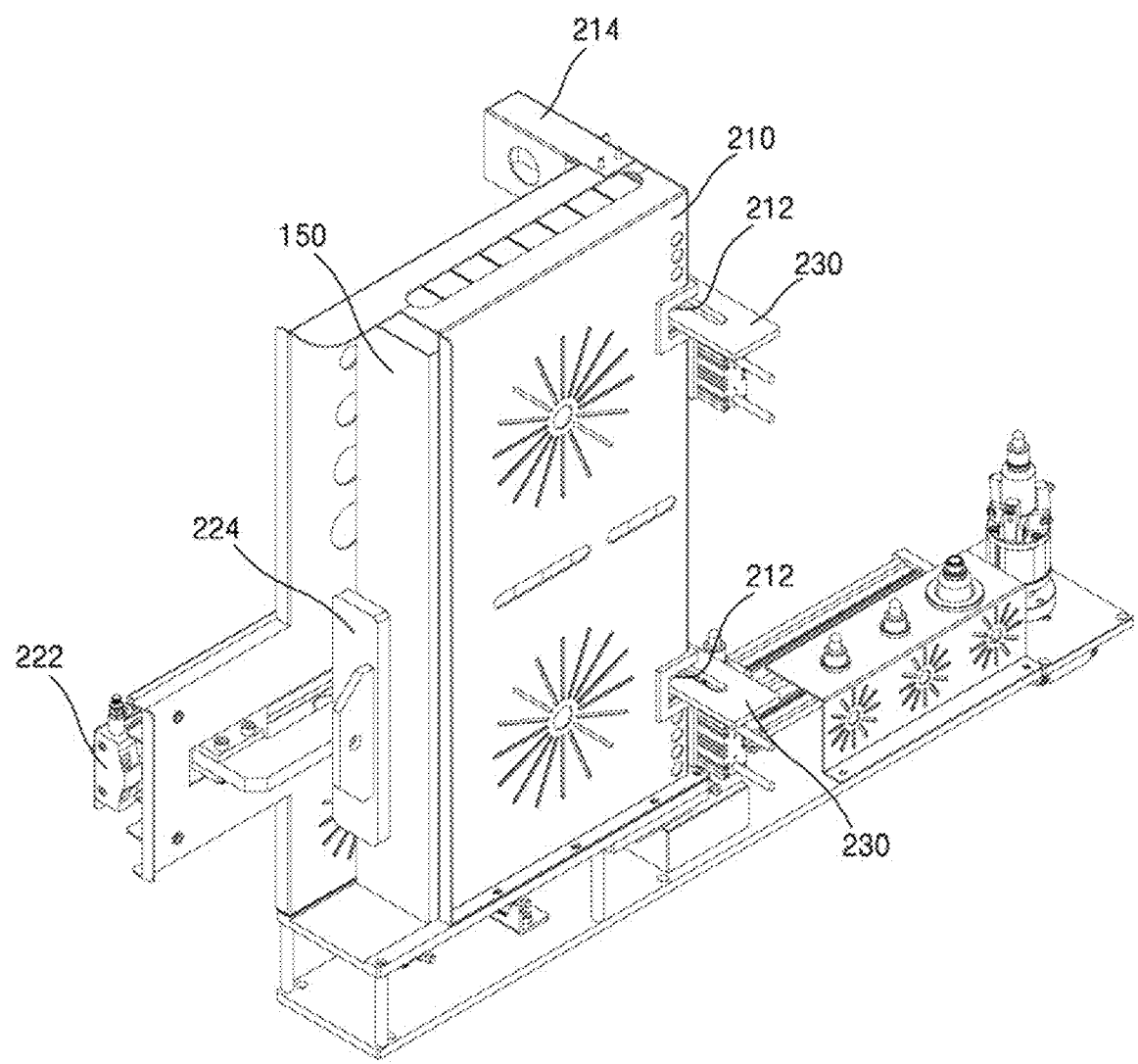
Figure 17:
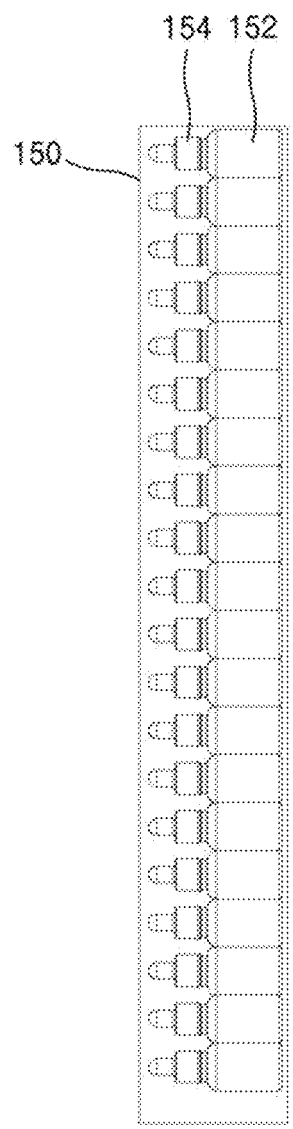
FIG. 17 is a cross-sectional view schematically illustrating an example of a cartridge supplied to the container supply part of FIG. 15.
Figure 18:
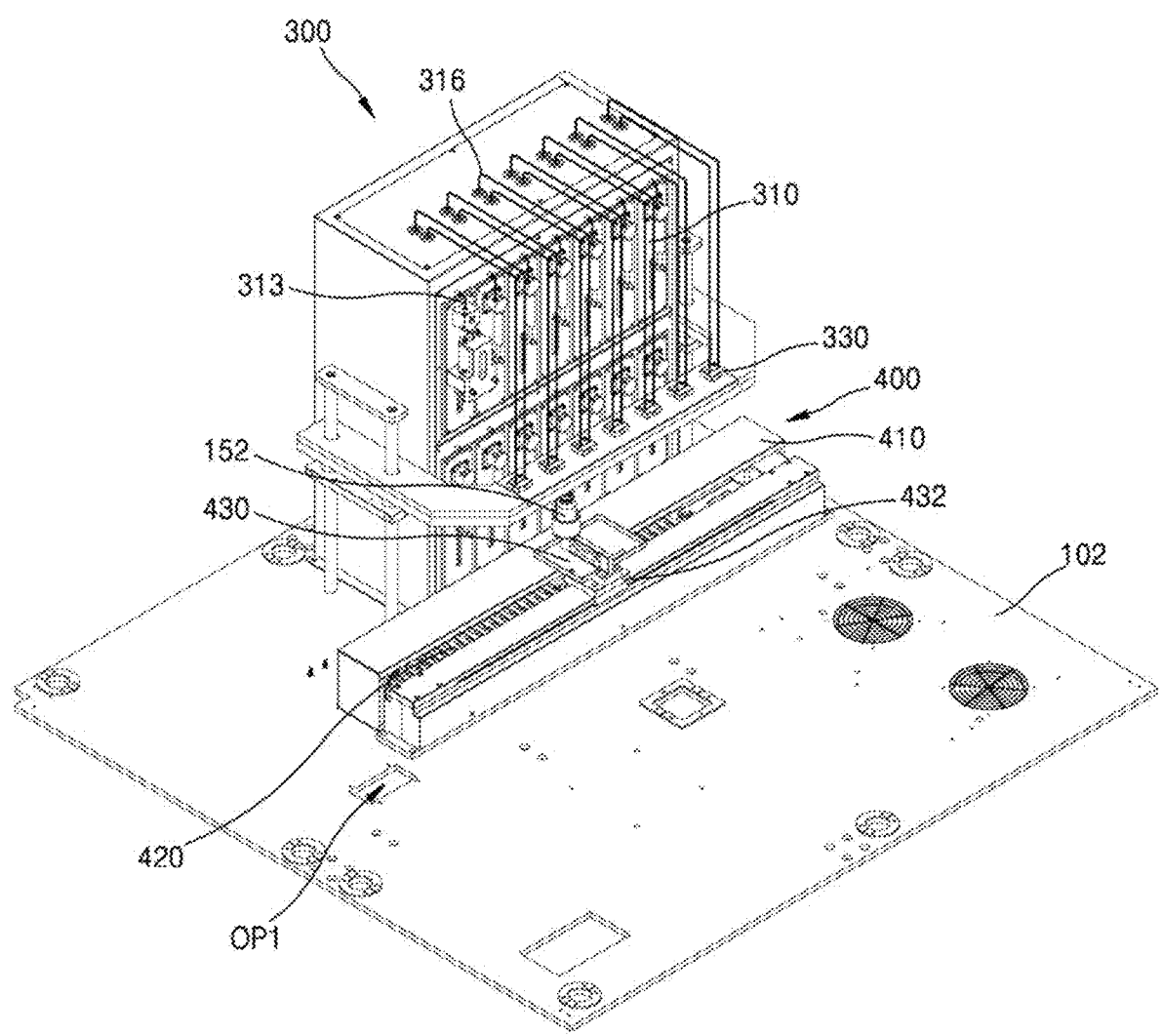
FIG. 18 is a perspective view schematically illustrating a raw material feeding part and a moving part of the apparatus for manufacturing the customized cosmetics of FIG. 13.
Figure 19:
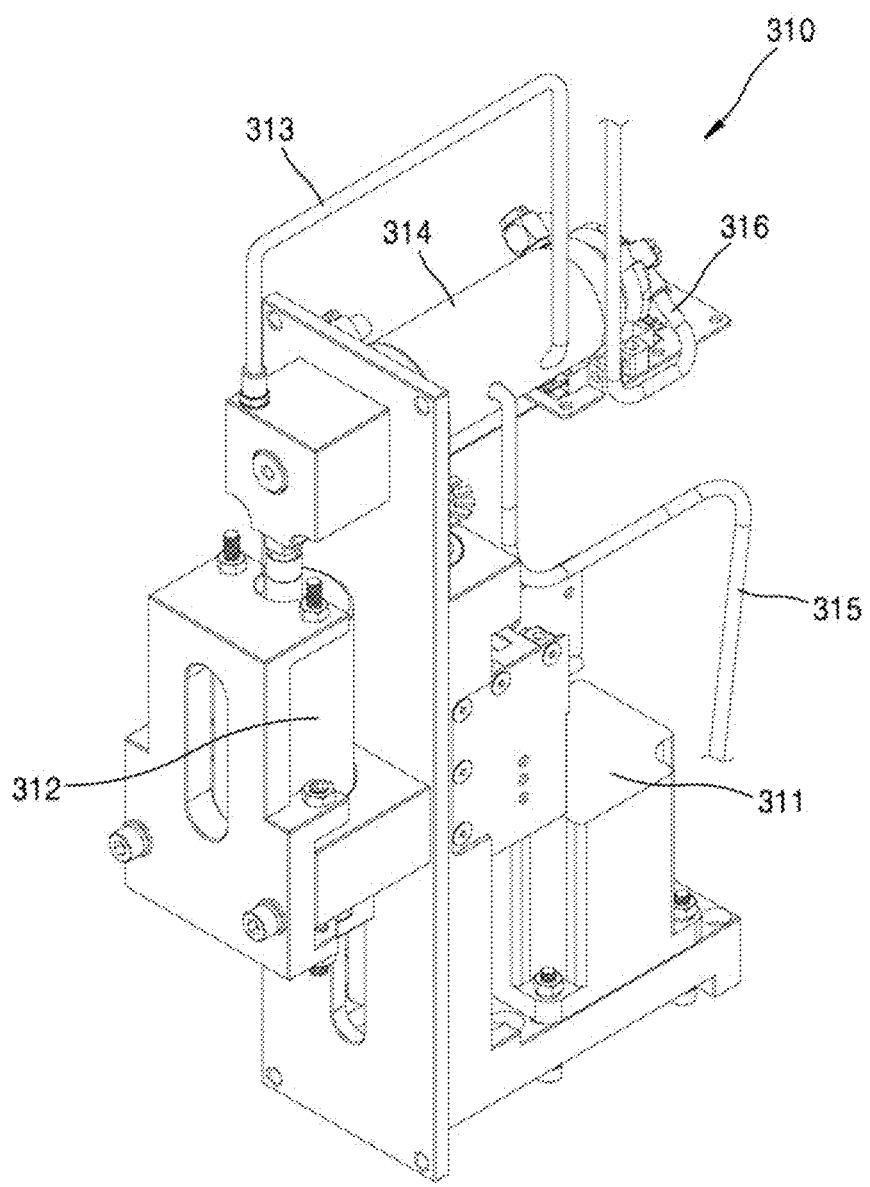
FIG. 19 is a perspective view schematically illustrating an example of a raw material feeding unit of the raw material feeding part of FIG. 18.
Figure 20:
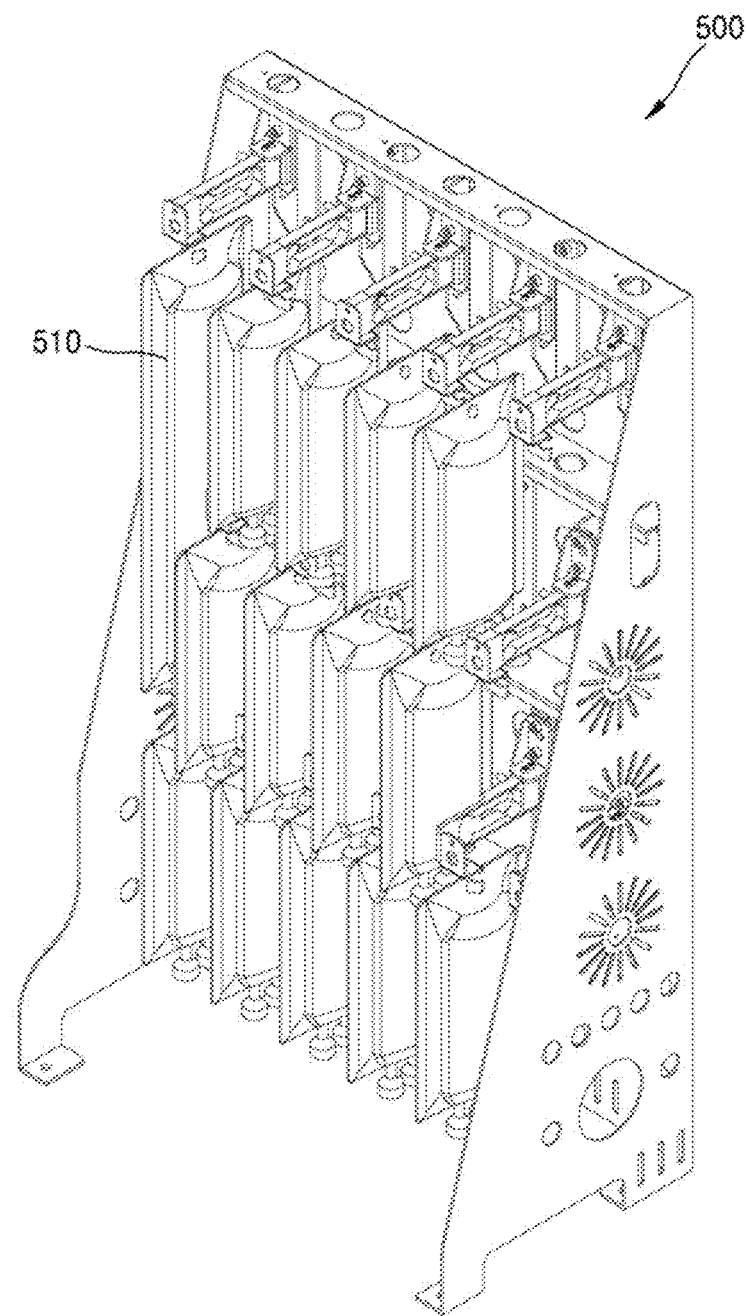
FIG. 20 is a perspective view schematically illustrating a raw material supply part of the apparatus for manufacturing the customized cosmetics of FIG. 13.
Figure 21:
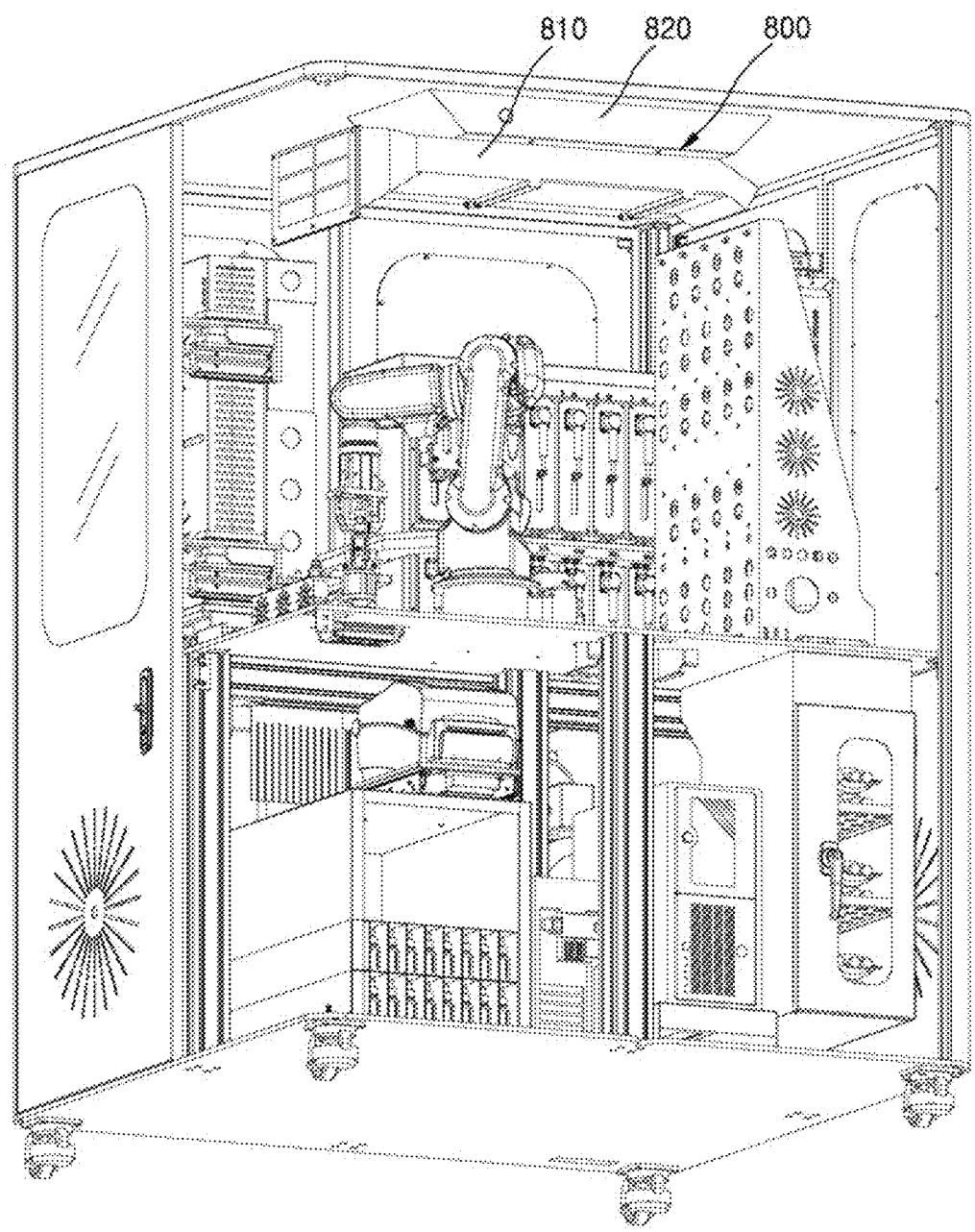
FIG. 21 is a perspective view schematically illustrating a part of the apparatus for manufacturing customized cosmetics of FIG. 13.

FIG. 13 is a perspective view schematically illustrating an apparatus for manufacturing customized cosmetics according to an embodiment of the disclosure. FIG. 14 is a perspective view schematically illustrating a part of the apparatus for manufacturing customized cosmetics of FIG. 13. FIGS. 15 and 16 are perspective views schematically illustrating a container supply part of the apparatus for manufacturing customized cosmetics of FIG. 13. FIG. 17 is a cross-sectional view schematically illustrating an example of a cartridge supplied to the container supply part of FIG. 15. FIG. 18 is a perspective view schematically illustrating a raw material feeding part and a moving part of the apparatus for manufacturing the customized cosmetics of FIG. 13. FIG. 19 is a perspective view schematically illustrating an example of a raw material feeding unit of the raw material feeding part of FIG. 18. FIG. 20 is a perspective view schematically illustrating a raw material supply part of the apparatus for manufacturing the customized cosmetics of FIG. 13. FIG. 21 is a perspective view schematically illustrating a part of the apparatus for manufacturing customized cosmetics of FIG. 13.

Referring to FIGS. 13 to 21, a customized cosmetic manufacturing apparatus 40 according to an embodiment of the disclosure includes a housing 100, a container supply part 200 for supplying a cosmetics container 152, a raw material feeding part 300 for feeding a cosmetic raw material into the cosmetics container 152, a transfer unit 400 for transferring the cosmetics container 152, a raw material supply part 500 for supplying a cosmetic raw material to the raw material feeding part 300, a robot arm 600 for moving the cosmetics container 152 to a required position step by step, and a controller 700 for controlling the operation of the customized cosmetic manufacturing apparatus 40. In addition, the customized cosmetic manufacturing apparatus 40 may include an air conditioner 800 for controlling internal temperature and air circulation and sterilizing the space inside the housing 100.

The housing 100 forms the exterior of the cosmetic manufacturing apparatus 40. For example, the housing 100 has a substantially hexahedral shape, and four pillars 110 are located at the four vertex positions of the hexahedral floor, and doors 120 are coupled to the four pillars 110 to form the sides of the hexahedron. That is, a pair of doors 120 may be located on each of the sides of the hexahedron. Accordingly, it is possible to prevent foreign substances from being mixed with the cosmetics during the manufacturing process of the cosmetics.

In addition, the pair of doors 120 may be opened and closed by pushing the doors forward or backward, and the inner space of the housing 100 can be opened by pushing the pair of doors 120. Accordingly, the replenishment of a cartridge 150 to the container supply part 200, the replacement of a raw material pack 510 of the raw material supply part 500 may be easily performed.

A cover 130 may be disposed on the upper surface of the housing 100 to cover the inner space of the housing 100. A duct 132 through which air in the inner space of the housing 100 is discharged, may be located in the cover 130.

On the other hand, a touch screen 124 is located on any one of the doors 120, and a user may order manufacturing of cosmetics using the touch screen 124. For example, the touch screen 124 is located on the first door 120a of the pair of doors 120 located in front of the cosmetic manufacturing apparatus 40, and a payment part 125 for payment when ordering and a receipt issuing part 126 may be located together with the first door 120a.

In addition, an outlet 128, through which the manufactured cosmetics are discharged, and a label outlet of a label issuing machine 140, through which a label printed thereon information such as the ingredients and manufacturing date of the manufactured cosmetics is issued, may be located on a second door 120b of the pair of doors 120 located in front of the customized cosmetic manufacturing apparatus 40.

In addition, transparent windows 122 are formed in all the doors 120 and the second door 120b except for the first door 120a where the touch screen 124 is located, so that the cosmetic manufacturing process can be observed in real time from the outside.

Meanwhile, the housing 100 may include a lower plate 101 and an upper plate 102 positioned between the lower plate 101 and the cover 130, and the inner space of the housing 100 may be divided into an upper space and a lower space.

On the lower plate 101, a power distribution box 103 for electrical connection of elements of the customized cosmetic manufacturing apparatus 40, the controller 700 for controlling the operation of the customized cosmetic manufacturing apparatus 40, a cartridge storage part 105 for storing a cartridge 150, a raw material storage part 104 for storing a cosmetic raw material, and a label issuer 140 may be located. In addition, a space V for collecting an empty cartridge 150a discharged from the container supply part 200 may be provided on the lower plate 101.

Elements for manufacturing cosmetics are arranged on the upper plate 102. In detail, the container supply part 200 for supplying the cosmetics container 152, the raw material feeding part 300 for feeding the cosmetic raw material into the cosmetics container 152, the transfer unit 400 for transferring the cosmetics container 152 to the raw material feeding part 300, the raw material supply part 500 for supplying a cosmetic raw material to the raw material feeding part 300, the robot arm 600 for moving the cosmetics container 152 to the required position step by step, a holder 260 capable of holding a lid 154 separated from the cosmetics container 152 during the manufacturing process of cosmetics, and a stirring part 700 for stirring the cosmetics container 152 in which the cosmetic raw material is fed, are located on the upper plate 102.

The container supply part 200 may include, as shown in FIGS. 15 and 16, a case 210 for accommodating a plurality of cartridges 150, a first push part 220 positioned on one surface of the case 210 to bring the plurality of cartridges 150 into close contact in one direction, a second push part 230 positioned on the side that intersects with one surface of the case 210 to push an empty cartridge in a direction perpendicular to the one surface of the case 210, a moving part 240 located under the case 210 and reciprocating in a direction parallel to the direction in which the plurality of cartridges 150 are in close contact with each other, and a seating part 250 on which the cosmetics container 152 discharged from the cartridge 150 is seated.

Meanwhile, as shown in FIG. 17, each of the plurality of cartridge 150 may be filled with a plurality of cosmetics container 152, the cosmetics container 152 filled in the cartridge 150 may be sequentially discharged through one side cross-section of the cartridge 150. The cosmetics container 152 may be filled in the cartridge 150 while the lid 154 is fastened thereto. For example, the lid 154 may include a dropper.

The cartridge 150, as shown in FIG. 16, may be inserted into the case 210 through a surface opposite to the surface on which the second push part 230 is located.

The first push part 220 may include a push rod 222 that is movable in the direction parallel to the direction in which the cartridges 150 are in close contact with each other, and a push arm 224 that is connected to the push rod 222 and is in close contact with an outermost cartridge from among the cartridges 150.

The push arm 224 may move together with the push rod 222 according to the movement of the push rod 222, and may push the cartridges 150 in one direction so that the cartridges 150 are in close contact with each other. At this time, in order to stably push the side of the cartridge 150, the push arm 224 my extend in the longitudinal direction of the cartridge 150 and thus may have a large area.

In order to insert the cartridge 150 into the case 210, the cartridge 150 may be inserted into the case 210 from the front of the push arm 224, while the push rod 222 is retracted. After inserting the cartridges 150 into the case 210, the push rod 222 may advance so that the push arm 224 can bring the cartridges 150 into close contact with each other.

Meanwhile, as shown in FIG. 15, the moving part 240 and the seating part 250 reciprocating in a direction parallel to the direction in which the cartridges 150 are in close contact with each other, are located in the lower space of the case 210. A seating hole 252 for accommodating the cosmetics container 152 may be formed in the seating part 250.

First, when the seating hole 252 is positioned under the cartridge 150, the cosmetics container 152 discharged from the cartridge 150 is seated, while lying, in the seating hole 252 of the seating part 250. More specifically, the seating hole 252 has such a size that the cosmetics container 152 is housed, and the lid 154 coupled to the cosmetics container 152 is housed in a hole of the moving part 240 which is continuously formed with the seating hole 252.

Afterwards, when the seating part 250 is moved to a position that does not overlap with the case 210 by the movement of the moving part 240, since the moving part 240 blocks the open lower surface of the cartridge 150, additional discharge of the cosmetics container 152 from the cartridge 150 is prevented.

Meanwhile, the seating part 250 is coupled with the rod 251 extending in a first direction, and by rotating the seating part 250 90 degrees around the rod 251 during movement, the cosmetics container 152 may have an erected state. At this time, since the seating hole 252 may accommodate only the cosmetics container 152 part, the lid 154 may protrude to the outside of the seating hole 252 in the state where the cosmetics container 152 is erected. The cosmetics container 152 being erected may be transported to the transfer unit 400 after the lid 154 is separated by the robot arm 600.

Referring back to FIG. 15, the empty cartridge 150a from which the cosmetics containers 152 are all discharged, may be discharged to the outside of the case 210 by the second push part 230. In an embodiment, a pair of second push parts 230 may be positioned to be spaced apart from each other on the side of the case 210 that intersects with one surface of the case 210 where the first push part 220 is positioned.

In addition, a guide hole 212 is formed, in a direction perpendicular to the first direction, on the side surface of the case 210 where the second push part 230 is located, and the second push part 230 is fastened to the guide hole 212 to perform a reciprocating motion along the guide hole 212.

In addition, on one surface of the case 210, a discharge guide 214 for guiding the movement of the empty cartridge 150a which is discharged may be formed. For example, the discharge guide 214 may have a shape with an open lower end, surrounding at least a portion of the upper surface and both side surfaces of the empty cartridge 150a to be discharged.

When the second push part 230 advances, the empty cartridge 150a may be pushed out of the case 210 following the discharge guide 214.

Meanwhile, as shown in FIG. 18, an opening OP1 may be formed in the upper plate 102, and the empty cartridge 150a discharged to the outside of the case 210 along the discharge guide 214 may fall into a space V for collecting the empty cartridge 150a on the lower plate 101 through the opening OP1.

The robot arm 600 separates the lid 154 protruding outside the seating hole 252 from the cosmetics container 152 while the cosmetics container 152 is erected, and stores the separated lid 154 in a holder 260, and then transfers the cosmetics container 152, from which the lid 154 is separated, to the transfer unit 400.

The robot arm 600 is located in the center of the upper plate 102, may rotate in place, and may have a multi-joint configuration. In addition, the robot arm 600 includes a gripper 602 capable of rotating and picking up, separates or couples the lid 154 from or to the cosmetics container 152, and picks up the cosmetics container 152 to the required position for each step.

The cosmetics container 152 transferred to the transfer unit 400 moves to be under a nozzle unit 330 of the raw material feeding part 300, and the nozzle unit 330 may allow necessary cosmetic raw materials to be injected into the cosmetics container 152 therethrough.

The transfer unit 400 may include a driving part 420, a support 410 in which the driving part 420 is located and which has an opening exposing the driving part 420 in the center portion thereof, and a support 430 on which the cosmetics container 152 is to be placed.

The support 430 may be coupled to a connecting part 432 fastened to the support 410 and the driving part 420. In an embodiment, the connecting part 432 may be bent in a "⊏" shape, and coupled to cover the upper end of the support 410 at one side of the opening, and simultaneously, coupled with the exposed driving part 420. Through the connecting part 432, the support 430 may reciprocate by the driving part 420. In an embodiment, the driving part 420 may be a conveyor belt, a chain, or the like.

The support 430 may include a weight sensor. For example, the weight sensor may be a load cell. Therefore, whether the correct amount is injected may be monitored in real time while the cosmetic raw material is injected into the cosmetics container 152.

The raw material feeding part 300 may include a plurality of raw material supply units 310 and a nozzle unit 330 through which the cosmetic raw material supplied from the plurality of raw material supply units 310 is injected into the cosmetics container 152.

FIG. 19 shows an example of the raw material supply parts 310. Referring to FIG. 19, the raw material supply part 310 may include a pump 311 for driving a syringe 312 and a cylinder 314 filled with a cosmetic raw material. A first pipe 313 through which the compression force by the syringe 312 is delivered into the cylinder 314, a second pipe 315 through which a cosmetic raw material supplied by the raw material supply part 500 is delivered into the syringe 312, and the third pipe 316 through which the cosmetic raw material inside the syringe 312 is delivered to the nozzle unit 330, may be connected to the cylinder 314.

Accordingly, the cosmetic raw material supplied by the raw material supply part 500 into the cylinder 314 through the second pipe 315 is moved to the nozzle unit 330 through the third pipe 316 by air injected into the cylinder 314 through the first pipe 313, thereby into the cosmetics container 152. The raw material supply part 310 may accurately supply a small amount of cosmetic raw material to the nozzle unit 330 through a syringe pump.

Meanwhile, although an embodiment using a syringe pump is illustrated and described in FIG. 19, the disclosure is not limited thereto. For example, the raw material supply part 310 may include various well-known elements such as a gear pump.

The nozzle unit 330 includes a plurality of nozzles respectively connected to the plurality of raw material supply units 310 through third pipes 316. Therefore, when the cosmetic raw material is injected into the cosmetics container 152, the cosmetics container 152 moves to be under the nozzle for injecting the cosmetic raw material among the plurality of nozzles by the transfer unit 400 to allow the cosmetic raw material to be injected into the cosmetics container 152 accurately.

The raw material supply part 500 includes a plurality of raw material packs 510 containing different cosmetic raw materials, and the plurality of raw material packs 510 may be connected to the raw material supply parts 310 through the second pipes 315. Accordingly, the number of the plurality of raw material packs 510 and the number of the plurality of raw material supply parts 310 may be the same. Meanwhile, in order to facilitate replacement of the raw material packs 510, the raw material supply part 500 may be arranged such that the plurality of raw material packs 510 face the door 120.

After the injection of the cosmetic raw material into the cosmetics container 152 is completed, the lid 154 stored in the holder 260 is combined with the cosmetics container 152 by the robot arm 600, and the cosmetics container 152 combined with the lid 154 is transferred to the stirring part 700.

The stirring part 700 fixes the position of the cosmetics container 152, and rotates in place to allow the cosmetic raw material in the cosmetics container 152 to be uniformly mixed.

After the stirring is completed, the cosmetics container 152 is transferred to the outlet 128 by the robot arm 600, and the cosmetics container 152 may be discharged to the outside through the outlet 128. In addition, the label issuing machine 140 may issue a label printed with cosmetic ingredients, expiration dates, manufacturing history information, and the like.

Meanwhile, as shown in FIG. 21, an air conditioner 800 connected to the duct 132 may be located under the cover 130.

The air conditioner 800 may include an air conditioner unit 810 having a fan for forcing the flow of air in one direction, and a plasma discharge unit 820 for sterilizing the space inside the housing 100. Therefore, the temperature inside the housing 100 may be kept constant.

In addition, the plasma generated by the plasma discharge unit 820 is diffused into the housing 100 during the operation of the air conditioner, and thus, highly reactive negative ions may be formed by the plasma in the housing 100. These anions have strong reducing properties. Accordingly, the anions are reduced into water by reacting with hydrogen cations in the cell membrane of microorganisms or viruses, and due to this process, the microorganisms and viruses are inactivated and thus the inner space of the housing 100 is sterilized.

The operation of the customized cosmetic manufacturing apparatus 40 may be controlled by the controller 700. The controller 700 controls the operation of the components described above. Also, the controller 700 may communicate with the measurement part 20 outside the customized cosmetic manufacturing apparatus 40 to receive information on the user's skin condition. In an embodiment, the measurement part 20 collects information on, for example, moisture content, dead skin cells, wrinkles, and skin tone of the user's skin and transmits the same to the controller 700, which controls the operation of the raw material feeding part 300 such that the type and amount of cosmetic raw materials are adjusted according to the received information to manufacture cosmetics customized for each user. For example, the controller 700 may select a cosmetic raw material or combine cosmetic raw materials at a certain mixture ratio, in consideration of the user's skin tone, pores, moisture content, and degree of pigmentation.

In addition, the controller 700 communicates with the external terminal, and may send information on the amount of cosmetics remaining in the raw material pack 510 of the raw material feeding part 300, the number of cartridges 150 in the container supply part 200, the temperature and humidity inside the customized cosmetic manufacturing apparatus 40, and may receive an operation command from the external terminal.

The controller 700 may be provided separately from the service providing server 30 to operate according to a processor 320 of the service providing server 30, and the service providing server 30 may be provided as the controller 700. According to an embodiment, the controller 700 may operate according to a processor of the skin diagnosis server 10 as well as the processor 320 of the service providing server 30.

The embodiment according to the disclosure may be implemented in the form of a computer program that can be executed through various elements on a computer, and such a computer program may be recorded in a computer-readable medium. In this case, the medium may store a program executable by a computer. Examples of the medium include a magnetic medium such as a hard disk, a floppy disk and a magnetic tape, an optical recording medium such as CD-ROM and DVD, a magneto-optical medium such as a floppy disk, and ROM, RAM, flash memory, and the like, which are configured to store program instructions.

Meanwhile, the computer program may be specially designed and configured for the disclosure, or may be known and used by those skilled in the computer software field. Examples of the computer program may include not only machine language code generated by a compiler, but also high-level language code that can be executed by a computer using an interpreter or the like.

In addition, although preferred embodiments of the disclosure have been illustrated and described above, the disclosure is not limited to the specific embodiments described above, and Various modifications can be made by those of ordinary skill in the art to which the disclosure pertains without departing from the gist of the disclosure as claimed in the claims, and these modifications should not be understood separately from the concept or perspective of the disclosure.

Therefore, the concept of the disclosure should not be limited to the embodiments, and not only the claims described below, but also all scopes equivalent to or changed therefrom belong to the scope of the concept of the disclosure.

The invention claimed is:

1. A method of providing customized cosmetic service and manufacturing customized cosmetics by using a customized cosmetic manufacturing apparatus, the customized cosmetic manufacturing apparatus comprising a raw material feeding part configured to feed a cosmetic raw material into a cosmetics container, a transfer unit configured to transfer the cosmetics container, and a controller configured to control an operation of the customized cosmetic manufacturing apparatus, wherein the transfer unit includes a driving part, and a support coupled to the driving part and on which the cosmetics container is to be placed, the method comprising:
obtaining skin measurement information and skin input information of a user by using a user terminal;
generating skin diagnosis information on a skin condition of the user based on the skin input information and the skin measurement information;
generating recipe data for manufacturing customized cosmetics based on the skin diagnosis information; and
manufacturing, by the customized cosmetic manufacturing apparatus, the customized cosmetics based on the recipe data, wherein the manufacturing comprises:
transferring, by the transfer unit, the cosmetics container on the support along a first direction, in which a plurality of raw material supply units included in the raw material feeding part are arranged; and
injecting, by the raw material feeding part, one or more cosmetic raw materials from the plurality of raw material supply units to the cosmetics container while the cosmetics container on the support reciprocates by the driving part along the first direction, and
wherein, the manufacturing further comprises, in the injecting, controlling an operation of the raw material feeding part such that a type and an amount of the one or more cosmetic raw materials are adjusted according to the recipe data that is customized for the user, and
wherein the method further comprises providing a non-face-to-face skin coaching service, wherein the providing of the non-face-to-face skin coaching service comprises:
matching an expert for each user;
obtaining coaching data generated by the expert based on the skin diagnosis information, the recipe data, and manufactured customized cosmetic information;
providing the coaching data to the user at a preset time and/or period; and
calculating a coaching cost based on service evaluation information obtained from the user, and providing the coaching cost to a matched expert.

2. The method of claim 1, wherein
the skin measurement information is obtained using a photographing part and a sensor part, and
the skin input information is obtained through a user input on a selection interface displaying a diagnosis check item, wherein the diagnosis check item includes at least one of an oily type diagnosis item, a pigment type diagnosis item, a moisture type diagnosis item, a wrinkle type diagnosis item, a pore type diagnosis item, a trouble diagnosis item, and a sensitivity diagnosis item.

3. The method of claim 1, wherein
the generating the skin diagnosis information comprises:
generating quantitative data for each skin variable by quantifying, with respect to each skin variable, the skin input information and the skin measurement information;
generating qualitative data including at least one of a skin type of the user, a detailed description of the skin type, care information suitable for the skin type, and skin age based on the skin measurement information and the skin input information; and
providing a skin diagnosis certificate indicating at least one of the quantitative data and the qualitative data.

4. The method of claim 3, wherein
the generating the recipe data comprises:
manufacturing a customized base by determining a first base amount of a solubilized base and a second base amount of an emulsified base according to the skin diagnosis information, wherein a first amount of the customized base is calculated by adding the first base amount and the second base amount;
determining whether to add a lipophilic component and a second amount according to the skin diagnosis information; and
determining an effective component and a third amount, wherein the effective component includes a component that manages each of a whitening item, a moisturizing item, an elasticity item, a wrinkles item, an acne item, a soothing item, a sebum control item, and a pore reduction item, wherein
transparency, texture, and formulation of customized cosmetics are determined based on at least one of the first amount, the second amount, and the third amount.

5. The method of claim 1, wherein
the support included in the transfer unit includes a weight sensor to monitor whether a correct amount of the one or more cosmetic raw materials is injected into the cosmetics container.

* * * * *